US007163823B2

(12) United States Patent
Patno et al.

(10) Patent No.: US 7,163,823 B2
(45) Date of Patent: Jan. 16, 2007

(54) DNA HYBRIDIZATION DEVICE AND METHOD

(75) Inventors: Timothy Patno, Chicago, IL (US); Mark Fisher, Highland Park, IL (US); George Kyaw Soe Maung, Chicago, IL (US); Tom Westberg, Gurnee, IL (US)

(73) Assignee: Nanosphere, Inc., Northbrook, IL (US)

( * ) Notice: Subject to any disclaimer, the term of this patent is extended or adjusted under 35 U.S.C. 154(b) by 266 days.

(21) Appl. No.: 10/352,714

(22) Filed: Jan. 27, 2003

(65) Prior Publication Data

US 2003/0224505 A1 Dec. 4, 2003

Related U.S. Application Data

(60) Provisional application No. 60/426,316, filed on Nov. 14, 2002, provisional application No. 60/352,346, filed on Jan. 28, 2002.

(51) Int. Cl.
*C12M 3/00* (2006.01)

(52) U.S. Cl. .............................. 435/287.2; 435/288.4; 422/101

(58) Field of Classification Search ............. 435/287.2, 435/288.3, 288.4, 305.3; 422/101
See application file for complete search history.

(56) References Cited

U.S. PATENT DOCUMENTS 3,745,091 A 7/1973 McCormick ............. 435/305.3
5,192,503 A 3/1993 McGrath et al. .............. 422/57
5,346,672 A 9/1994 Stapleton et al. ........... 422/102
5,571,721 A 11/1996 Turner ..................... 435/305.1
5,605,813 A 2/1997 Stevens et al. .......... 435/40.52
5,741,463 A 4/1998 Sanadi ....................... 422/101
6,143,496 A 11/2000 Brown et al. .................. 435/6
6,159,727 A 12/2000 Bochkariov .............. 435/287.2
6,258,593 B1 * 7/2001 Schembri et al. ........ 435/287.2
6,475,774 B1 11/2002 Gupta ..................... 435/287.2
6,514,750 B1 2/2003 Bordenkircher et al. . 435/286.2
2001/0046702 A1 11/2001 Schembri ................. 435/287.2
2002/0001839 A1 1/2002 Schembri ................. 435/287.2
2002/0048754 A1 4/2002 Lockhart et al. ............... 435/6
2002/0095073 A1 7/2002 Jacobs et al. ............... 600/300
2003/0013164 A1 1/2003 Streit et al. .............. 435/287.2

OTHER PUBLICATIONS

Supplementary Search Report for European Patent Application No. 03713303.0-2113, completed Feb. 16, 2006, mailed Mar. 3, 2006.

* cited by examiner

*Primary Examiner*—David Redding
(74) *Attorney, Agent, or Firm*—McDonnell Boehnen Hulbert & Berghoff LLP

(57) ABSTRACT

An apparatus and method for DNA hybridization is provided. The apparatus and method work in conjunction with a substrate comprising an upper surface having probes. The apparatus may comprise a material which abuts the substrate, with at least a portion of the material being pliable. The material and the substrate form a plurality of chambers, each chamber having a bottom including at least a portion of the upper surface, at least one sidewall, and an opening. The apparatus further comprises a mechanism for closing the openings of the chambers, thereby sealing the chambers.

31 Claims, 26 Drawing Sheets

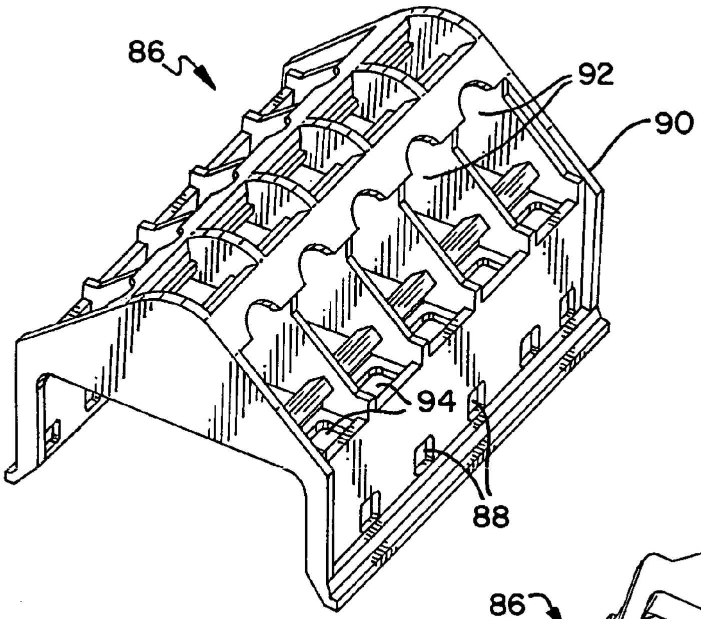
FIG. 4a
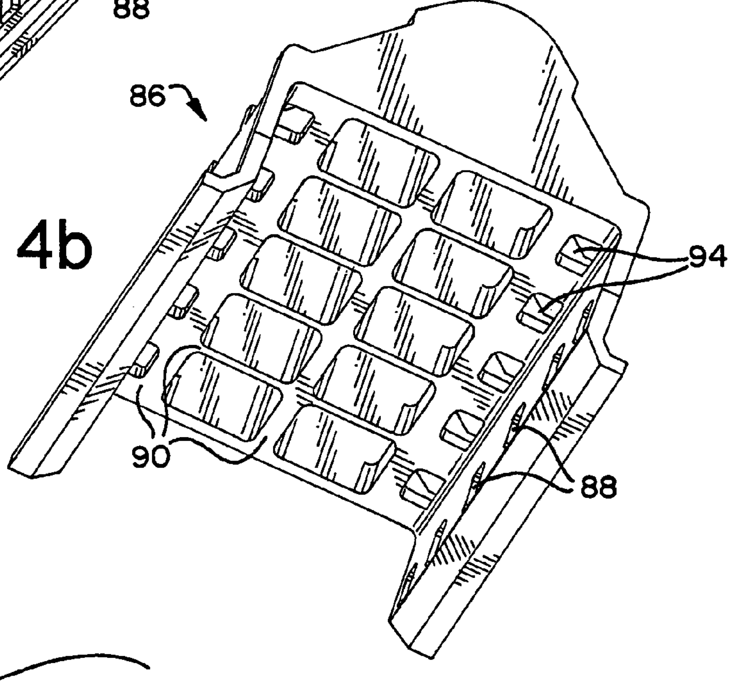
FIG. 4b
FIG. 5
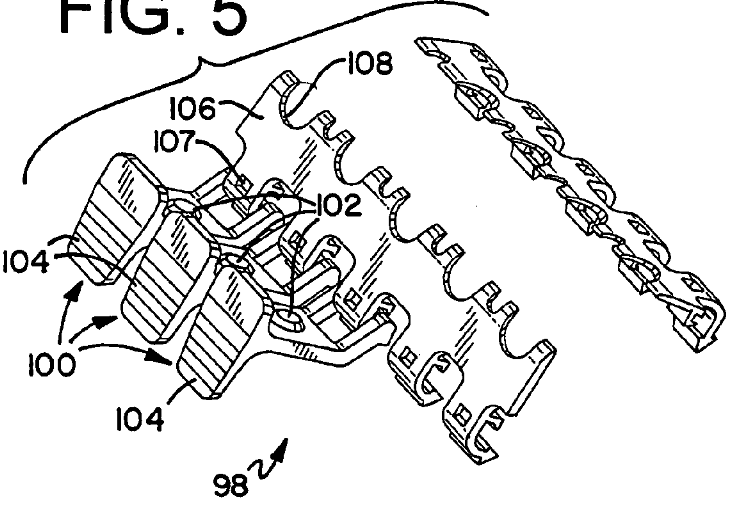

FIG. 6a
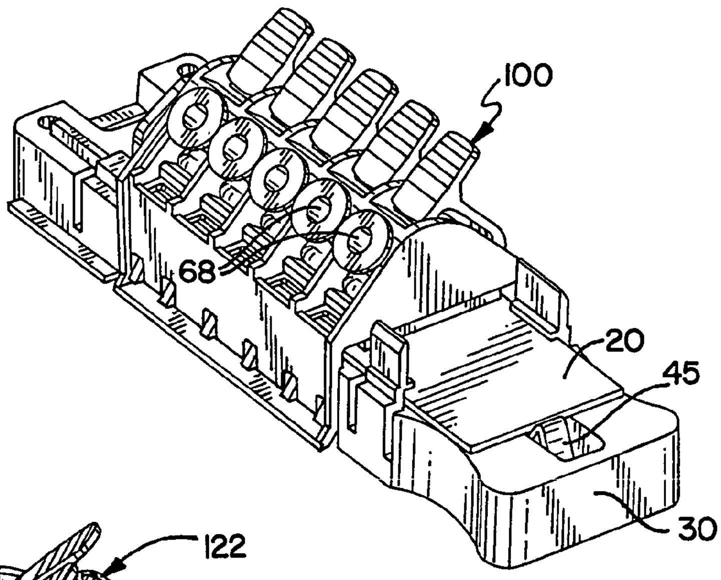
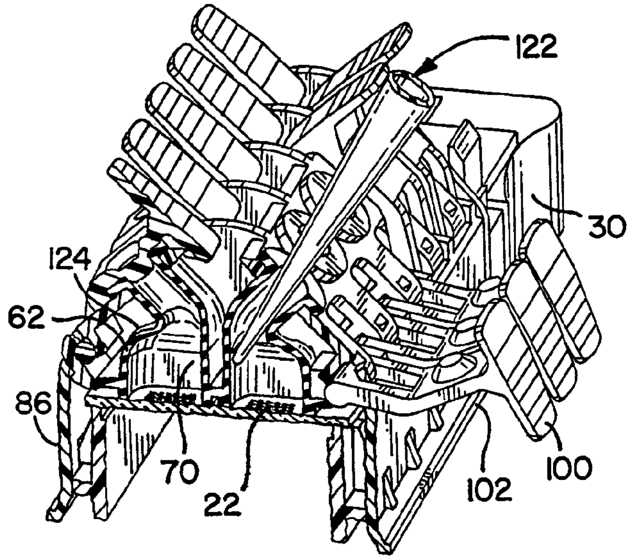
FIG. 6b
FIG. 6c
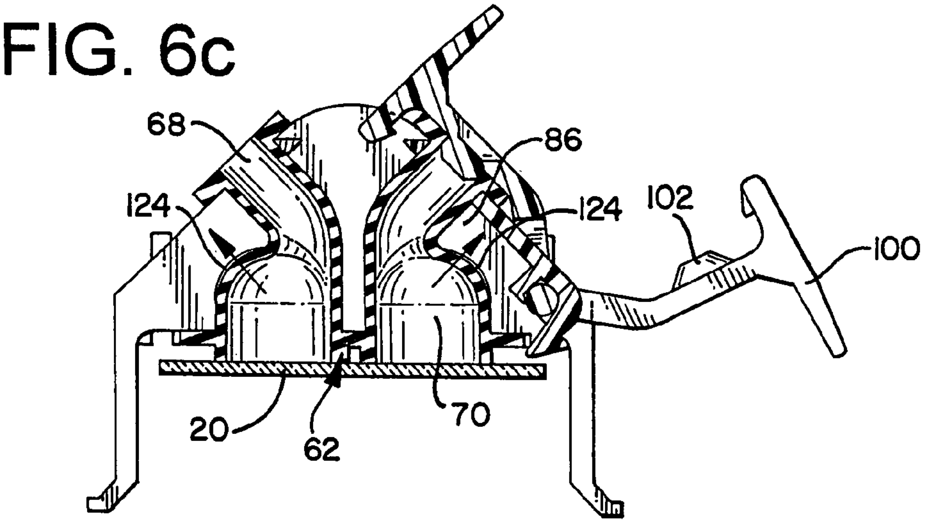

FIG. 17a

PRIOR ART PROCESS

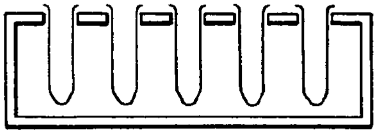

PREPARATION AND COLLECTION OF ALL EQUIPMENT: DRY ICE FOR ICE BATH, MICROCENTRIFUGE TUBES PLACED IN RACKS AND SOLUTIONS READY TO USE ETC.

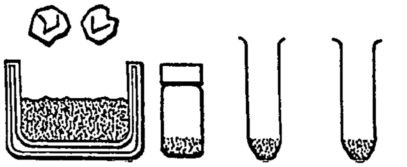

THE TUBES THAT ARE USED FOR MIXING OF THE TEST SOLUTIONS ARE PLACED AND ARRANGED IN A TUBE TRAY.

THERE ARE TEN TUBES, FOR TEN TESTS. THE TUBES CORRESPOND TO THE TEN TESTS THAT RESIDE ON THE SLIDE.

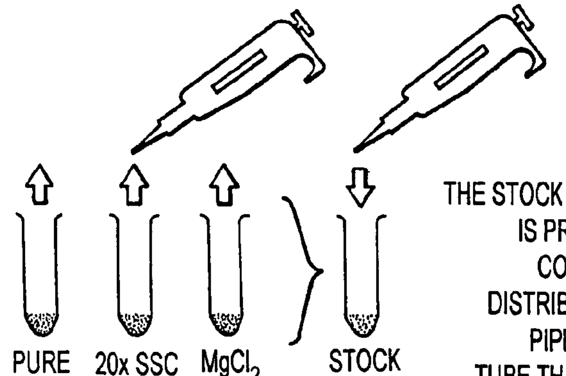

THE STOCK OR MASTER MIX IS PREPARED IN ONE CONTAINER AND IS DISTRIBUTED BY MICRO PIPETTE INTO EACH TUBE THAT REQUIRES IT.

NOT ALL TUBES NECESSARILY REQUIRE THE STOCK, AS EACH TUBE REPRESENTS A DIFFERENT TEST.

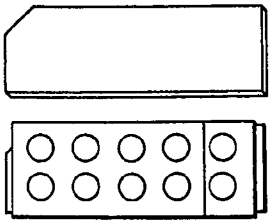

THE SLIDE IS REMOVED FROM THE DECANTER.

THE SLIDE IS CARRIED BY HAND. THE SLIDE HAS A CORNER NOTCH WHICH KEYS THE SLIDE'S ORIENTATION.

THE SLIDE HAS THEN APPLIED TO IT (BY HAND) A RUBBER GASKET SEAL WHICH HAVE HOLES TO ALLOW FOR THE SOLUTION TO BE PLACED IN CONTACT WITH THE DOTS. THE HOLES IN THE RUBBER GASKET ACT AS "WELLS" FOR THE SOLUTION.

PROCESS WITH HYBRIDIZATION CHAMBERS

U UNCHANGED

M THE TUBES ARE PREARRANGED INTO A SINGLE PREORDERED NEST. THERE IS ONE SINGLE TUBE NEST FOR ONE SLIDE.

U UNCHANGED

X THIS STEP IS ELIMINATED

FIG. 17b

| PRIOR ART PROCESS | PROCESS WITH HYBRIDIZATION CHAMBERS |
| --- | --- |
| 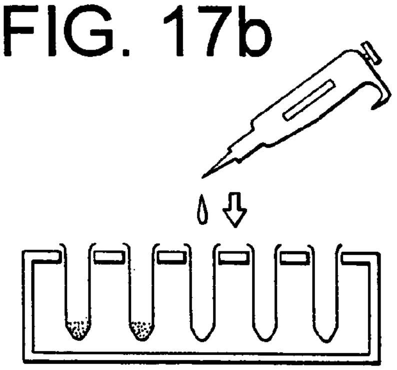 THE TUBES HAVE ALL THEIR RESPECTIVE COMPONENTS ADDED BY MICRO PIPETTE. | U UNCHANGED |
| 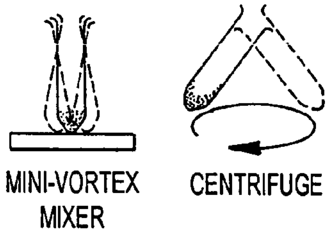  ALL THE TUBES ARE THEN VORTEXED AND THEN SPUN DOWN WITH A SMALL CENTRIFUGE BUILT TO RECEIVE ABOUT 6-8 MICRO CENTRIFUGE TUBES.<br><br>THE PROCESS ALWAYS OCCURS IN THE ORDER: VORTEXING THEN SPINNING. THE VORTEXING MIXES THE SOLUTION AND THE CENTRIFUGAL SPINNING FORCES, CAUSES THE SOLUTION TO DEPOSIT AT THE BOTTOM OF THE TUBE FOR EASY EXTRACTION WITH A MICRO PIPETTE. | THE SINGLE NEST IS VORTEXED AND CENTRIFUGED TOGETHER. X POTENTIAL SPATIAL MAPPING PROBLEMS ARE ELIMINATED.<br>M A SPECIAL CENTRIFUGE INSERT MAY BE USED TO ACCEPT THE TUBE NEST. |
| 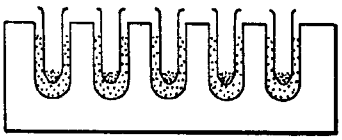 THE TUBES ARE THEN REMOVED FROM THE CENTRIFUGE AND PLACED INTO A PREVIOUSLY PREPARED HEAT BATH. THE TUBES ARE LEFT THERE FOR 5 MINS. | X THE SINGLE TUBE NEST IS THEN PLACED IN A HEAT BATH.<br>M |
| 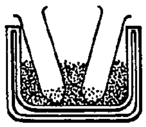 THE TUBES ARE THEN REMOVED FROM THE HEAT BATH AND IMMEDIATELY PLACED INTO A PREVIOUSLY PREPARED ICE BATH. THE TUBES ARE "SNAP FROZEN" FOR 1 MINUTE. | X THE SINGLE TUBE NEST IS THEN PLACED IN A ICE BATH.<br>M |
| 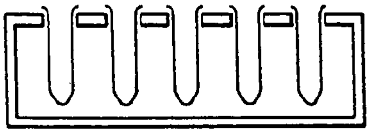 THE TUBES ARE REMOVED FROM THE ICE BATH AND PLACED INTO A TRAY AND ALLOWED TO THAW FOR 5 MINS. | U UNCHANGED |

FIG. 17c

| PRIOR ART PROCESS | PROCESS WITH HYBRIDIZATION CHAMBERS |
|---|---|
| THE TUBES AFTER THAWING FOR 5 MINS, ARE INDIVIDUALLY VORTEXED AND SPUN DOWN. THEY ARE LEFT TO REST IN A TUBE TRAY. | X THE SINGLE TUBE NEST IS VORTEXED. M |
| THE CAREFULLY PREPARED MIXED SOLUTIONS ARE THEN TRANSFERRED FROM EACH TUBE INTO EACH RELEVANT TEST WELL ON THE SLIDE. | X SNAPPING THE SLIDE ONTO THE TUBE NEST ELIMINATES THIS TRANSFER. |
| THE SLIDE IS NOW TAKEN TO THE ENVIRONMENTAL CHAMBER. THE DOTS AND THE SOLUTIONS ARE GIVEN TIME TO REACT WHILE IN THE CHAMBER. THE TEST IS BEING PERFORMED WHILE IN INCUBATION. | M THE SINGLE TUBE NEST IS TRANSFERRED TO THE ENVIRONMENTAL CHAMBER. THE TUBE NEST DESIGN CAN ACCOMMODATE A HEATED WATER BATH TO SUBSTITUTE THE ENVIRONMENTAL CHAMBER. |

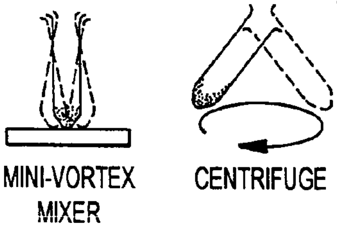

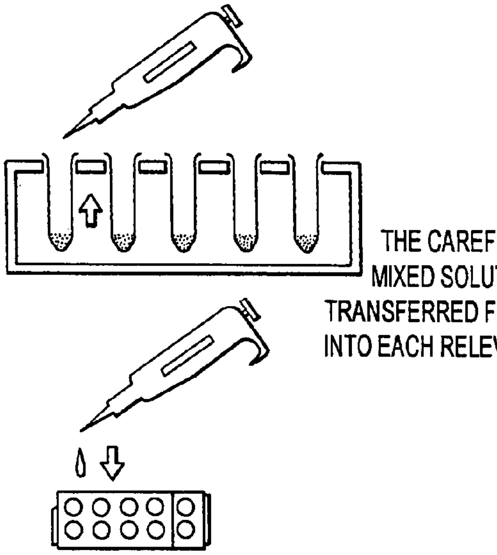

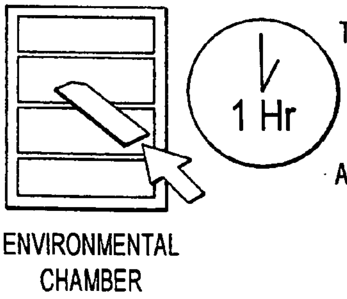

FIG. 17d

| PRIOR ART PROCESS | PROCESS WITH HYBRIDIZATION CHAMBERS |
|---|---|
| THE GASKET IS NOW REMOVED TO ALLOW THE "WASH" STAGES TO COMMENCE. | X THERE IS NO GASKET TO BE REMOVED. |
| THE BIOCHEMICAL PROCESS THAT OCCURRED DURING THE INCUBATION PERIOD CAUSES THE RESULTS OF THE TEST TO BE "COVALENTLY BONDED" TO THE SLIDE. | M THE WASH STAGES CAN OCCUR WITHIN THE WELLS OF THE TUBE NEST REDUCING POSSIBILITY OF CROSS-CONTAMINATION. |
| THE SLIDE IS NOW WASHED.<br><br>THE FIRST WASH REQUIRES THAT THE SLIDE IS BATHED IN 1M OF NaNo3 (1 MOLE OF SODIUM SOMETHING) FOR A CERTAIN NUMBER OF SECONDS. | M THE WASH STAGES CAN OCCUR WITHIN THE WELLS OF THE TUBE NEST REDUCING POSSIBILITY OF CROSS-CONTAMINATION. |
| THE SLIDE IS THEN BATHED IN A SECOND WASHING STEP, THE SILVER WASH FOR A CERTAIN AMOUNT OF TIME. | M THE WASH STAGES CAN OCCUR WITHIN THE WELLS OF THE TUBE NEST REDUCING POSSIBILITY OF CROSS-CONTAMINATION. |
| THE SLIDE IS THEN TREATED TO A PURE WATER WASHING STAGE FOR CLEANING OFF ANY RESIDUAL SILVER WASH SOLUTION. THE SILVER CAN "DEVELOP" IN UNDESIRABLE PLACES ON THE SLIDE, LATER CONFUSING THE OPTICAL SCAN.<br><br>THIS STAGE IS REPEATED THREE TIMES. | M THE WASH STAGES CAN OCCUR WITHIN THE WELLS OF THE TUBE NEST REDUCING POSSIBILITY OF CROSS-CONTAMINATION.<br><br>THE SLIDE CAN BE REMOVED FROM THE TUBE NEST AT THIS POINT.<br><br>THE SLIDE IS READY TO BE SCANNED. |

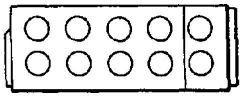

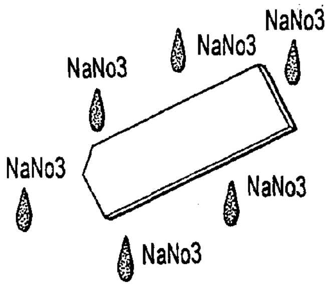

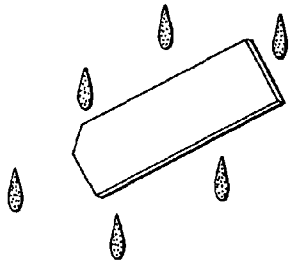

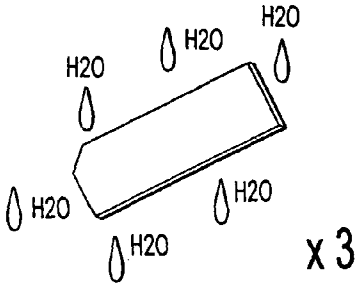

HYBRIDIZATION BATH PREPARATION

TRACKING SLIDE AND IMAGING ON NIS-2000

DNA HYBRIDIZATION DEVICE AND METHOD

REFERENCE TO RELATED APPLICATIONS

The current patent application claims priority to U.S. patent application Ser. No. 60/352,346 filed on Jan. 28, 2002 and entitled "DNA Hybridization Device and Method." The current patent application also claims priority to U.S. patent application Ser. No. 60/426,316 filed on Nov. 14, 2002 and entitled "DNA Hybridization Device and Method." This application incorporates by reference U.S. patent application Ser. No. 60/352,346 and U.S. patent application Ser. No. 60/426,316 in their entirety.

FIELD OF THE INVENTION

This present invention relates to hybridization. More specifically, the invention provides for methods and apparatuses for hybridization of DNA.

BACKGROUND OF THE INVENTION

Sequence-selective DNA detection has become increasingly important as scientists unravel the genetic basis of disease and use this new information to improve medical diagnosis and treatment. DNA hybridization tests on oligonucleotide-modified substrates are commonly used to detect the presence of specific DNA sequences in solution. The developing promise of combinatorial DNA arrays for probing genetic information illustrates the importance of these heterogeneous sequence assays to future science.

Typically, the samples are placed on or in a substrate material that facilitates the hybridization test. These substrate materials can be glass or polymer microscope slides or glass or polymer microtiter plates. One example of a probe includes capture probes, such as DNA capture probes. Organization of the tests on a substrate may occur by laying out areas of circular patterns of concentrated capture strand DNA in nominal sizes between 100 and 500 microns. As shown in FIG. 1, there are 10 areas on the substrate. More or less areas may be used depending on the needs of experiments. Further organization may occur by placing spots with different synthetic DNA sequences in a common area that is exposed to the same sample. In particular, there may be a plurality of the same or different types or probes in an area on the substrate.

The DNA hybridization test may thus include: synthetic DNA capture strands immobilized on a substrate; a strand of target DNA; and a probe. Specifically, one such technique for DNA hybridization is the chip based DNA detection method that employs probes. A probe may use synthetic strands of DNA complementary to specific targets. Attached to the synthetic strands of DNA is a signal mechanism. If the signal is present (i.e., there is a presence of the signal mechanism), then the synthetic strand has bound to DNA in the sample so that one may conclude that the target DNA is in the sample. Likewise, the absence of the signal results (i.e., there is no presence of the signal mechanism) indicates that no target DNA is present in the sample. Thus, a system is needed to reliably detect the signal and accurately report the results.

One example of a signal mechanism is a gold nanoparticle probe with a relatively small diameter (10 to 40 nm), modified with oligonucleotides, to indicate the presence of a particular DNA sequence hybridized on a substrate in a three component sandwich assay format. See U.S. Pat. No. 6,361,944 entitled "Nanoparticles having oligonucleotides attached thereto and uses therefore," herein incorporated by reference in its entirety; see also T. A. Taton, C. A. Mirkin, R. L. Letsinger, *Science,* 289, 1757 (2000). The selectivity of these hybridized nanoparticle probes for complementary over mismatched DNA sequences was intrinsically higher than that of fluorophore-labeled probes due to the uniquely sharp dissociation (or "melting") of the nanoparticles from the surface of the array. In addition, enlarging the array-bound nanoparticles by gold-promoted reduction of silver(I) permitted the arrays to be imaged in black-and-white by a flatbed scanner with greater sensitivity than typically observed by confocal fluorescent imaging of fluorescently labeled gene chips. The scanometric method was successfully applied to DNA mismatch identification.

To execute the DNA hybridization, the user should locate together complementary strands of synthetic DNA with the target DNA at a specified temperature and humidity. The temperature should be closely controlled so that only the DNA of choice hybridizes, which increases the test's selectivity. Controlling the humidity is thus important as the fluid volumes used in the test are in the microliters range.

In order to process the test, the user should interact several reagents at very small volumes. Micropipettes may be used to transfer reagents from their storage containers into mixing containers. The mixing container is much larger than the fluid volumes used so a centrifugation step is necessary to condense all the solution into one area of the container. This mixing container must also be humidity and temperature controlled so it must be a closed environment that can be immersed in or placed on a medium that is maintained at the desirable hybridization temperature. One may use microfuge tubes, racks, an environmental chamber, water baths, vortexing machines and mini-centrifuges to execute this process.

In the prior art, the hybridized target DNA/signal mechanism (such as gold nanoparticle DNA) is added to a slide using a micropipette to transfer the solution from the mixing container to the slide. In this prior art method, a gasket is manually applied to the microscope slide using adhesive. A second hybridization step now occurs with the solution on the slide inserted into an environmental chamber to maintain the slides temperature and humidity. The slide is removed from the environmental chamber following the second hybridization and the excess fluid/unbound DNA is removed by washing the slide in a water-based wash solution.

The last step may be the addition of a signal amplification solution, which may precipitate a metal onto the signal mechanism. This process should occur with a controlled temperature, humidity and light conditions as the solution is very reactive to light and temperature. Once this step is complete, the metal precipitate solution is removed from the slide by a second water-based wash solution.

These steps used in the prior art are complex, but the process can be manually controlled when only a single sample is being tested. However, a typical scenario is for many different samples to be run through the process in parallel. This results in high amounts of complexity as many tubes laid out in rack systems must all be tracked by the user as they sequentially remove the correct volumes of solutions from each tube and placed it in another corresponding tube or in a specific area of the hybridization slide. It is common for mistakes in micropipetting, spatial mapping or task sequencing to render a DNA hybridization test useless. The prior art manual process is also difficult to control thermally.

Accordingly, it would be advantageous to have a device and a method that would allow a simplification of the above process.

SUMMARY OF THE INVENTION

In one embodiment of the invention, an apparatus for DNA hybridization is provided. The apparatus works in conjunction with a substrate comprising an upper surface having probes. The apparatus may comprise a material which abuts the substrate, with at least a portion of the material being pliable. The material and the substrate form a plurality of chambers, each chamber having a bottom including at least a portion of the upper surface, at least one sidewall, and an opening. The apparatus further comprises a mechanism for closing the openings of the chambers, thereby sealing the chambers.

In one aspect, the sidewalls may be at least partially curved, such as where the sidewalls meet. The sidewalls may also be perpendicular or non-perpendicular (such as curved) to the surface of the substrate. In addition, the material may further comprise a neck portion providing a conduit for fluid from the opening to an inner portion of the chamber, where the neck portion has a first end connected to the opening and a second end connected to the inner portion. The neck portion may have an angle which is less than 180 degrees (such as an angle greater than 90 degrees and less than 180 degrees). Moreover, the second end of the neck portion may be off-center to the area enclosed within the sidewalls (i.e., centered at a point which is not directly above a geometric center of an area enclosed within the sidewalls).

In addition, the partially pliable material may be composed of a silicone-based material. The partially pliable material may further include at least one compression rib, with the compression rib contacting the upper surface of the substrate to form a seal around a circumference of at least one of the areas having probes.

The at least partially pliable material may abut the substrate in a variety of ways. One such way is by placing a rigid material which abuts with the partially pliable material. The rigid material may then be attached (either permanently or temporarily) with the substrate or with another material which holds the substrate, such as a substrate holder, so that the pliable material may form a seal with the upper surface of the substrate. The rigid material may, in one embodiment, act as a cover for the pliable material and may abut only a portion of the material. For example, an airspace may be formed between the rigid material and the at least partially pliable material (such as between one of the sidewalls and the rigid material). In this manner, the sidewall may expand into the airspace in order to reduce pressure within the chamber. The rigid material may further provide structure for the openings of the chamber. The pliable material may include an opening lip, the opening lip being adjacent to the opening, so that the rigid material may abut at least a portion of the opening lip to provide structure for the opening.

In addition, a rigid material may abut at least a portion of the substrate. In one aspect, the rigid material may comprise a substrate holder. The substrate holder may position the substrate in x-, y-, and/or z-directions. For example, the substrate holder may position the substrate, via springs, to a predetermined position such as a datum point. In one aspect, the substrate holder may be connected, either temporarily (such as via a snap) or permanently (such as via a hinge) to the cover.

The mechanism for closing the openings may comprise protrusions that can be inserted into the openings thereby sealing the chambers. The protrusions may be attached to one another (such as attached two or more protrusions together) and may be attached to the cover. Alternatively, the mechanism for closing the openings may pinch the opening, thereby sealing the chambers. One example of pinching the opening is be slotting the opening into a v-shaped groove.

BRIEF DESCRIPTION OF THE DRAWINGS

FIG. 4*a* is a top perspective view of one embodiment of a cover.

FIG. 4*b* is a bottom perspective view of one embodiment of the cover of FIG. 4*a*.

FIG. 5 is a perspective view of a face seal assembly, used in combination with the cover of FIG. 4*a*, for sealing the openings in the gasket.

FIG. 6*a* is a perspective view of the substrate, substrate holder, gasket and cover of FIG. 4*a*, and face seal assembly.

FIG. 6*b* is a perspective view of the substrate, substrate holder, gasket and cover of FIG. 4*a*, and face seal assembly, with one end of the device shown in cross-section.

FIG. 6*c* is a cross-sectional view of the substrate, substrate holder, gasket and cover of FIG. 4*a*, and face seal assembly.

FIGS. 17*a–d* is a flow chart comparing a prior art process with the process using hybridization chambers.

DETAILED DESCRIPTION OF PREFERRED EMBODIMENTS

As discussed in the background section, hybridization should be performed under precise temperature and humidity conditions. The hybridization may comprise, in one aspect, capture probes bound to a substrate. The capture probes may be DNA capture probes, as discussed in the background section. Alternatively, the capture probes may be RNA capture probes. The capture probes may form a complex with a target analyte. The target analyte may be a nucleic or non-nucleic acid. The target analyte may further bind to a detection probe, such as a nanoparticle detection probe, as discussed in the background section. The hybridization may comprise, in another aspect, target analyte(s) bound to a substrate. The target analyte (e.g., nucleic or non-nucleic acid) may thus form a complex with a capture probe, and may further bind with a detection probe, such as a nanoparticle detection probe.

Prior art devices used for hybridization of a substrate resulted in difficulties in controlling conditions effective for hybridization or created the possibility of cross contamination of different areas on the substrate. Thus, one embodiment of the invention is directed to a hybridization device that creates contained or sealed chambers for at least a part of a surface of the substrate. One example of a part of a surface of the substrate may comprise one of the areas on the substrate which contain capture probes. The hybridization chambers formed may comprise a part of the surface of the substrate, sidewalls and a top. The design of and materials for the hybridization chambers are to assist in efficient and effective hybridization tests, including DNA hybridization tests. Goals of the hybridization chamber include, but are not limited to: (1) protecting the substrate from physical damage; (2) making the contents of the well visible; (3) simplify handling of the substrate throughout the process; (4) rapidly heating the contents of the wells; (5) getting the fluid onto the slide instead of other portions on the hybridization chamber; (6) forming a seal between the slide and the sidewalls of the hybridization chamber; and (7) making the hybridization chamber airtight or nearly airtight.

Figure 1:
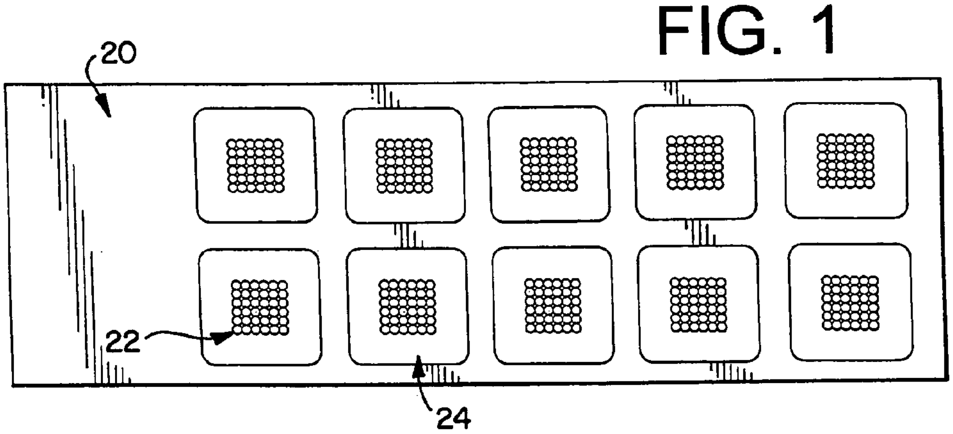
FIG. 1 is a top view of a substrate with a plurality of areas containing probes.

The presently preferred embodiments of the invention will now be described by reference to the accompanying figures, wherein like elements are referred to by like numerals. As shown in FIG. 1, a substrate 20 may contain a plurality of areas 24 of interest for testing. For example, the areas 24 may contain probes 22 bound to the substrate, such as DNA or RNA capture probes. Alternatively, the areas 24 on the substrate may contain target analytes bound to the substrate. The areas 24 are typically evenly spaced on a surface of a substrate (such as a slide). The hybridization device acts in conjunction with the substrate to create contained or sealed chambers for the plurality of areas. The chambers are formed in part by the areas on the substrate and in part by the hybridization device. As merely one example, each of the areas 24 may be a square (7 mm by 7 mm). The probes 22 may be centered within area 24 with dimensions of approximately 4.5 mm by 4.5 mm. The number of probes 22 in area 24 may vary depending on design. In one embodiment, the probes may be 6 by 6 (6 across a row and 6 in a column for a total of 36 probes in an area).

In one aspect, a chamber is formed with a bottom of the chamber (including at least a part of the surface of the substrate, such as one of the areas 24 of substrate 20), sidewalls, an opening and a mechanism to seal the opening (such as a protrusion to seal the opening or a device to pinch the opening shut). In one embodiment, the chamber(s) may be formed using a hybridization device, which includes a device to hold the substrate and a pliable material which abuts the substrate. The device to hold the substrate may comprise a substrate holder, examples of which are shown in FIGS. 2*a*–2*d* and 9*a*.

Figure 14B:
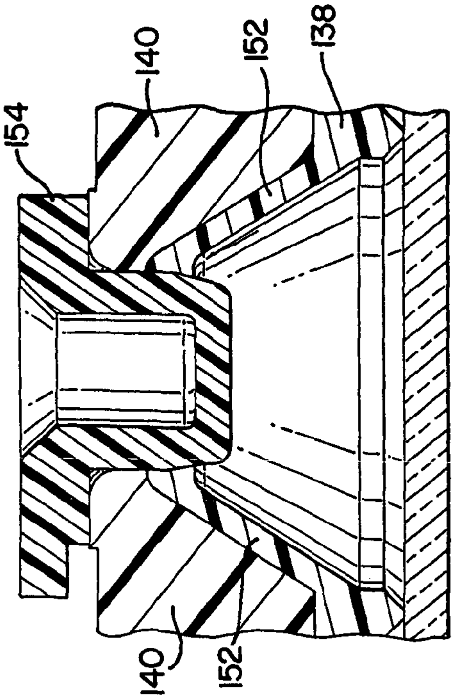
FIG. 14*b* is a cross-sectional view of a substrate, one embodiment of a hybridization chamber, opening and protrusion.
Figure 14A:
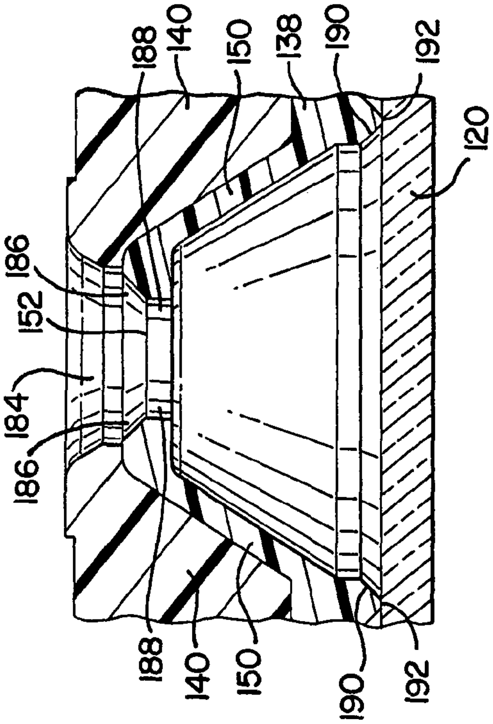
FIG. 14*a* is a cross-sectional view of a substrate, one embodiment of a hybridization chamber, and opening.

The pliable material which abuts the substrate may comprise a gasket, examples of which are shown in FIGS. 3*a–c* and 9*a*. The pliable material may include at least one sidewall (either in the form of one continuous curved sidewall or more than one sidewall) and an opening. The opening, as shown in FIG. 6*b* or 14*a*, may be at the uppermost portion of the hybridization chamber. Alternatively, the opening may be situated at another portion of the hybridization chamber, such as in one of the sidewalls.

The pliable material may abut the substrate to form a seal with the substrate in a variety of manners. In one embodiment, as discussed in more detail below, the pliable material may be pressed against the substrate using a rigid material. One example of this rigid material may be a cover, as shown, for example, in FIGS. 4*b* and 5, which presses the gasket against the substrate. Another example of this may include rigid materials, such as rigid material 40 shown in FIGS. 9*a*–9*b*. Alternatively, the pliable material may be glued to the substrate.

The hybridization device may further include a mechanism to seal the opening(s) in the chambers. The mechanism to seal the opening may be protrusion (such as a cap), which can be inserted in the opening to fill the opening, thus sealing or containing the chamber. Alternatively, the mechanism to seal the opening may be rigid material, which can be used to pinch or close the opening. In this manner, the area on the substrate may be contained thus allowing for easier processing including humidity control, as discussed subsequently in more detail. The hybridization device may then create chambers around at least some (and preferably all) of the areas on the substrate.

Figure 7A:
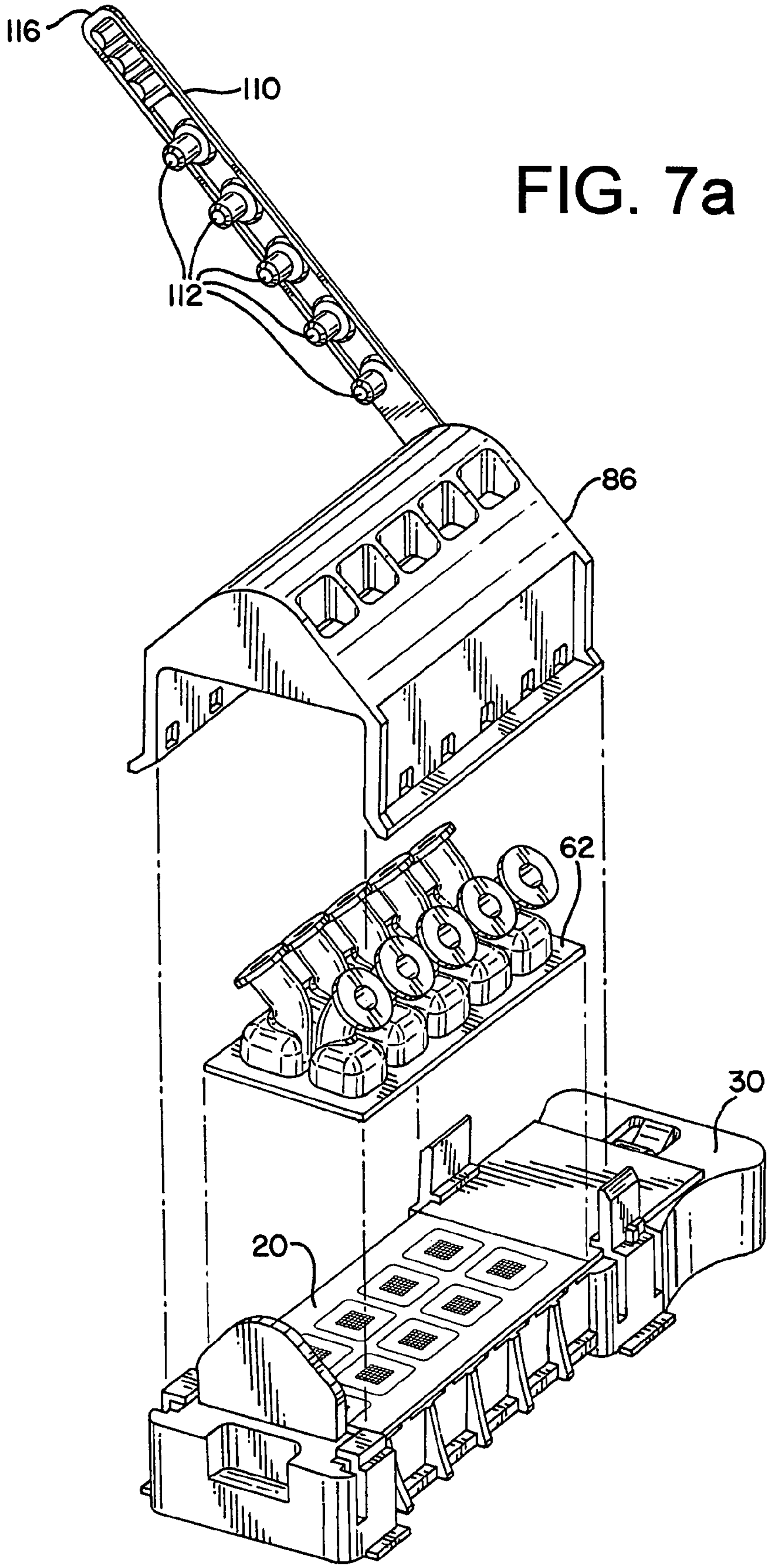
FIG. 7*a* is an exploded view of the substrate and substrate holder, gasket, cover of FIG. 4*a* and strip caps of FIG. 5*b*.
Figure 7B:
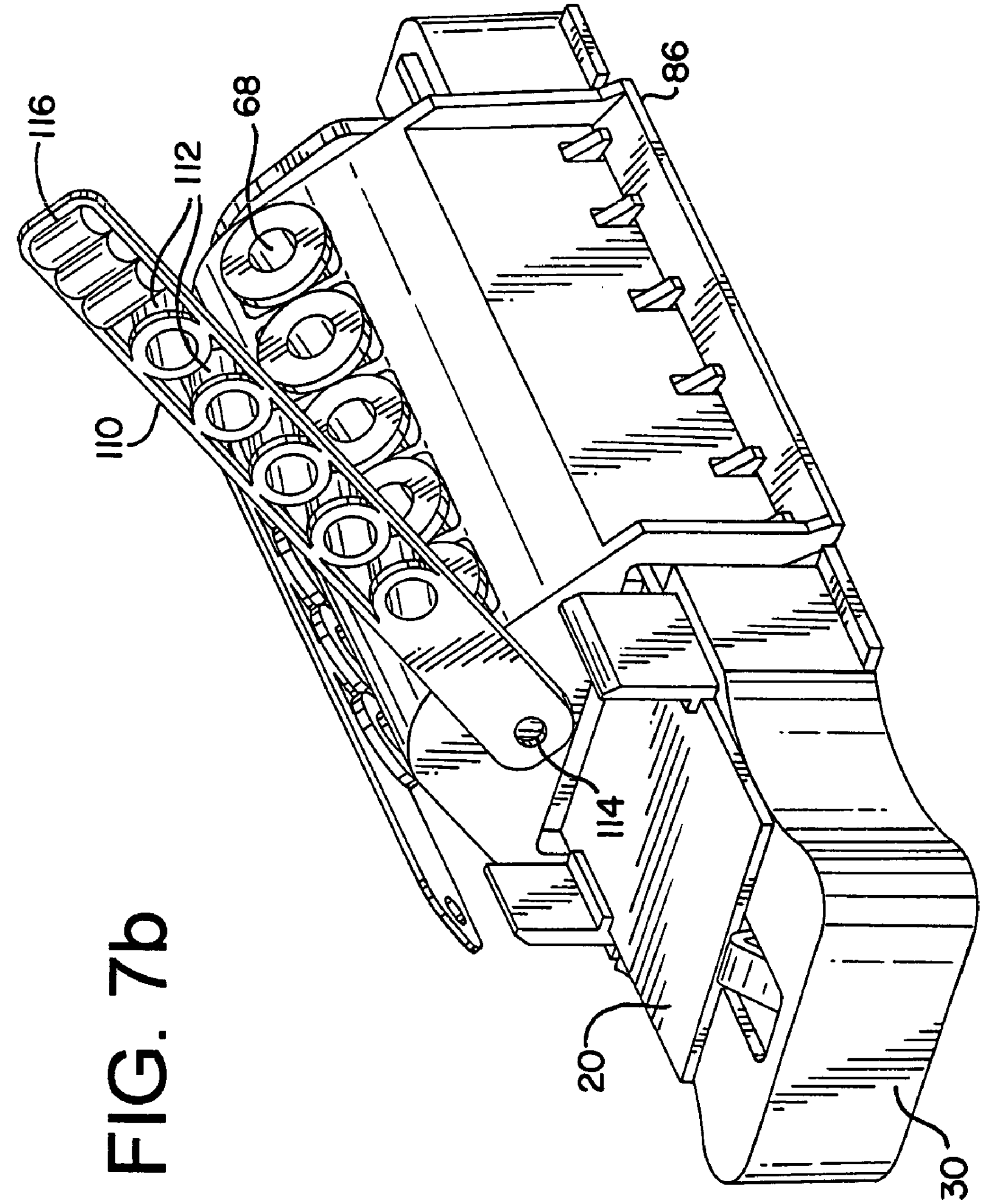
FIG. 7*b* is a perspective view of the substrate and substrate holder, gasket, cover of FIG. 4*a* and strip caps of FIG. 5*b*.

In one embodiment, the hybridization device may comprise a substrate holder, a gasket, a cover and a mechanism to seal the openings in the gaskets (such as the face seal assembly, shown in FIG. 5, or the strip caps, shown in FIG. 7*b*). Alternatively, the hybridization device may comprise a substrate holder, a gasket, and a cover (with the mechanism to seal the openings in the gaskets incorporated into the cover) (such as the pinch seal assembly, shown in FIG. 4*b*).

Figure 2A:
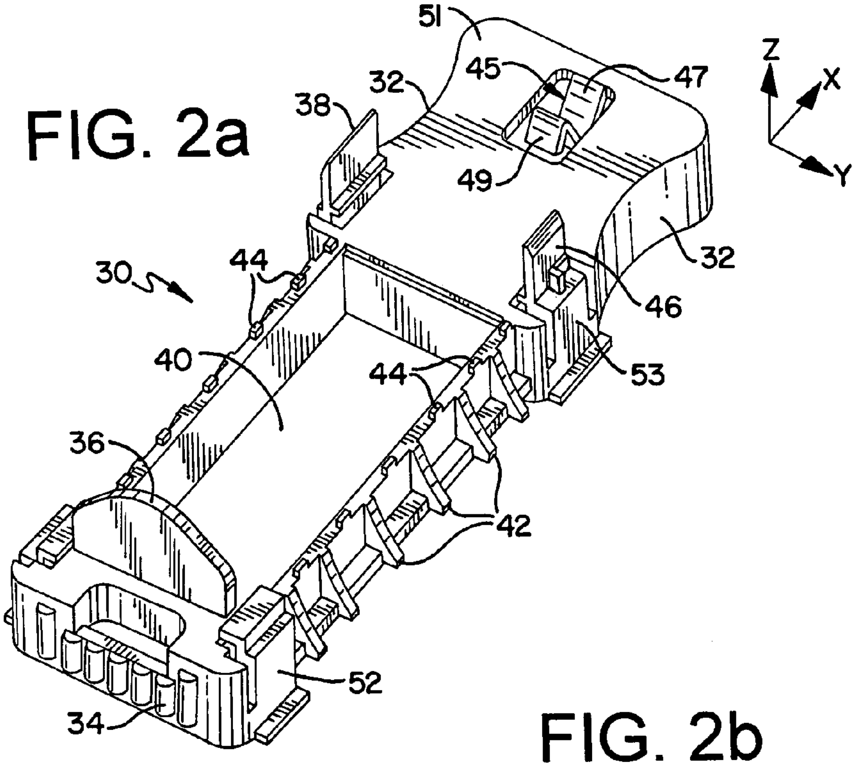
FIG. 2*a* is a perspective view of a substrate holder.
Figure 2B:
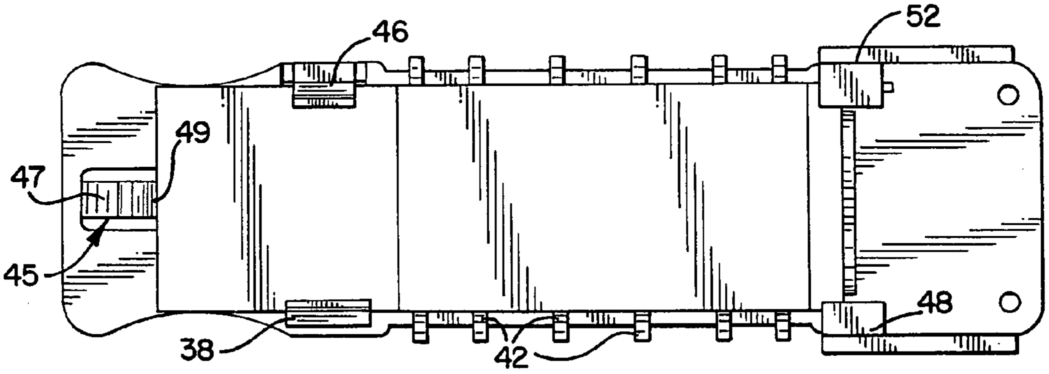
FIG. 2*b* is a top view of the substrate holder of FIG. 2*a*, the substrate holder holding a substrate.

Referring to FIGS. 2*a*–2*b*, there are shown perspective and top views of substrate holder 30. Substrate holder 30 may allow for (1) easier handling of the substrate; (2) protection of the substrate from damage (such as from breaking and scratches and/or contamination due to inadvertent touching); (3) proper alignment of the substrate (such as when using an analyzer to determine binding events on the surface of the substrate); and (4) potential integration with an analyzer, such as an optical imaging system, without interfering with optical imaging. Typically, the substrate 20 is a thin piece of glass, which is difficult to handle when trying to process the sample, such as shown in FIGS. 18*a*–18*e*, or when trying to analyze the sample, such as shown in FIG. 18*f*. Substrate holder 30 may be composed of a rigid material, such as polycarbonate, which may ease in the handling of substrate 20. Moreover, substrate holder may better protect the substrate 20 from damage. Contacting the probes 22 on the substrate 20, such as by touching the probes, may adversely affect the results of the experiments. Using a substrate holder reduces the possibility of directly contacting the probes on the substrate. Finally, the substrate holder may position the substrate in a predetermined position (such as a predetermined position in the x-, y-, and/or z-directions). In one embodiment, the position is predetermined in the x-, y- and z-directions. Alternatively, the position may be predetermined in any one or any combination of the three different directions. Predetermined positioning may assist in proper placement for the analyzing device and may allow for the creation of the wells around the areas 22 of substrate 20.

Substrate holder 30 includes curves 32 in order to grip the substrate holder 30. Substrate holder further includes ridges 34 which allows for gripping of an end of the substrate holder 30. Substrate holder also allows for stacking of substrates, as shown in FIG. 18*e*. Raised portion 36 may aid in stacking of the substrate holders on top of one another. Further, raised portion 36 may aid in protecting the substrate; held within substrate holder 30, from damage. Bracket 38 further allows for stacking of the substrate holders. Bracket 38 also enables positioning of the substrate 20 within substrate holder 30, which is discussed below.

Substrate holder 30 includes an opening 40, for unobstructed viewing of the substrate even when placed within substrate holder 30. For strength, substrate holder includes reinforcing strips 42 which provide for structural stiffening of the substrate holder 30 and which may be used to engage cover, as discussed below.

The substrate 20 may be inserted into the substrate holder 30 in a variety of ways. One such method is by sliding the substrate 20 from one end 51 of the substrate 30 until the substrate contacts hard stop 48, as discussed below. Ridges 44 serve to aid in positioning the substrate 20 within substrate holder 30, when sliding the substrate through the substrate holder 30. Ridges further serve to more evenly heat the substrate 20 within substrate holder 30. When sliding a substrate 20 into the substrate holder, ridges 44 allow for less resistance. Ridges 44 may be partly curved on the upper portion, reducing the surface area on which one side of the substrate contacts the substrate holder. Further, ridges 44 allow for air or water to enter more easily on the underside of the substrate (such as shown in FIG. 18*c*), enabling more even heating of the substrate.

As the substrate 20 is slid through substrate holder 30, it may engage a variety of clamps, guides, pins (such as guide pins 160 discussed below) which may position the substrate in substrate holder. One such guide is substrate retention snap 45. The substrate retention snap 45, at one end, is v-shaped 47. At the other end, the substrate retention snap 45 has teeth 49 for ratcheting the substrate into position. As the substrate is pushed in the x-direction, the teeth 49 of the substrate retention snap 45 are engaged. Force of the teeth 49 against the substrate 20 is maintained by the spring-like action of the v-shaped end 47. This enables the substrate to maintain its position in the x-direction.

Figure 2C:
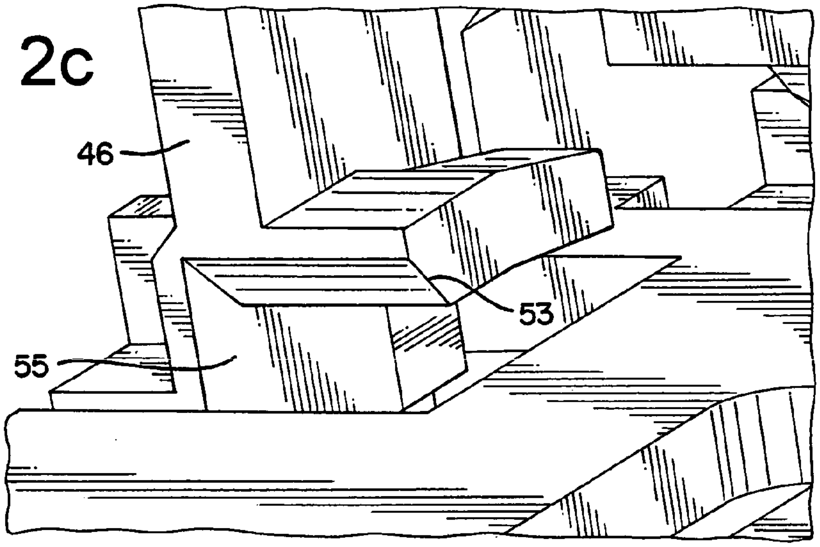
FIG. 2*c* is a perspective view of a bracket of the substrate holder of FIG. 2*a*.

Another such guide is shown in FIG. 2*c*, which is a perspective view of one end of the substrate holder of FIG. 2*a*. FIG. 2*c* illustrates a side view of flexible bracket 46. Flexible bracket has a spring-like action. Flexible bracket 46 is connected to substrate holder 30 at a point which is different from where the substrate 20 contacts flexible bracket 46. In this manner, flexible bracket may move in a direction perpendicular to the substrate. This is in contrast to bracket 38 which does not move (or does not appreciably move) in the direction perpendicular to the substrate. Bracket 38, similar to hard stop 48 discussed below, is connected to substrate holder 30 at the point where the substrate 20 contacts bracket 38. Thus, bracket 38 will not appreciably move in the y-direction. Flexible bracket 46 may include a chamfer in one or several directions. As shown in FIG. 2*c*, flexible bracket 46 may include a chamber in two directions. Chamfer 53, which is graduated in the downward, guides the substrate downward in the z-direction. Similarly, chamfer 55, which is graduated in the inward to the opening 40 of the substrate holder 30, guides the substrate inward in the y-direction. In this manner, the substrate 20 may be guided using flexible bracket 46. Chamfers may also be used on bracket 38, hard stop 48 and flexible bracket 52. Other means may be used to guide the substrate. For example, the brackets 38, 46, 52 or hard stop 48 may include a wishbone strip. Wishbone strip allows for the guiding of the substrate in one direction, such as the z-direction. For example, wishbone strip may have a spring action which, when a substrate is pushed in the x-direction, pushes the substrate in a downward direction (the z-direction)

Figure 2D:
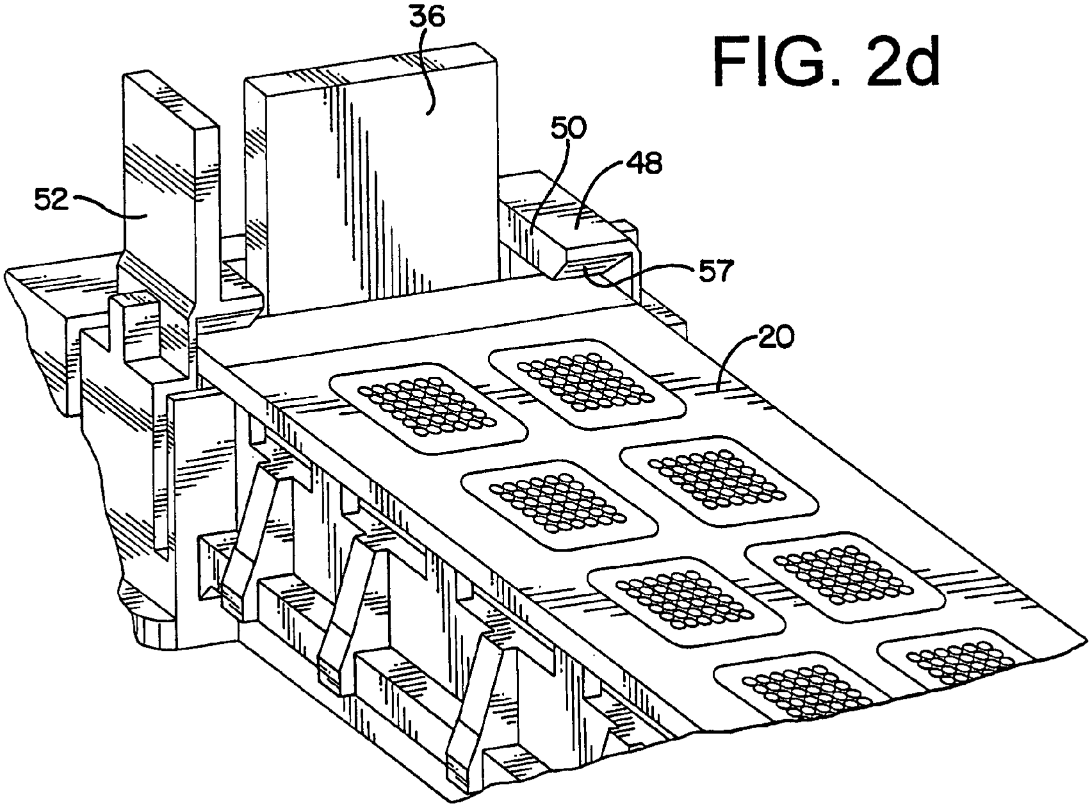
FIG. 2*d* is a perspective view of one end of the substrate holder holding a substrate.

Referring to FIG. 2*d*, there is shown a perspective view of the other end of the substrate holder of FIG. 2*a*. As shown in FIG. 2*d*, one end of substrate holder 30 has a hard stop 48. Hard stop 48 is the portion where the substrate should be pushed. The hard stop may act as a datum point. It may be composed of an inflexible material. Hard stop 48 may further include an upper lip 50, for the upper surface of the substrate to contact. As discussed above, hard stop 48 may include a chamfer 57 to guide the substrate. By contrast, flexible bracket 52, opposite of hard stop 48 as shown in FIG. 2*d*, may move in one direction (as shown in FIG. 2*d*, the y-direction). Flexible bracket 52 is connected at a section of substrate holder 30 which is lower than the point where flexible bracket 52 contacts the substrate 20. In this manner, flexible bracket 52 may move, pushing substrate 20 into hard stop 48. In addition, flexible bracket 52 includes an upper lip 54 which allows for proper placement in the z-direction. Thus, similar to flexible bracket 46, flexible bracket 52 pushes the substrate in the y-direction.

Figure 3A:
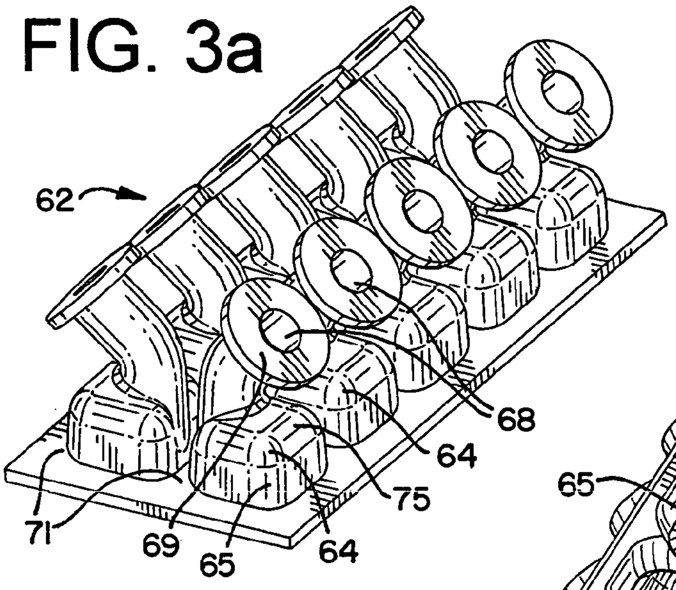
FIG. 3*a* is a top perspective view of a gasket.
Figure 3B:
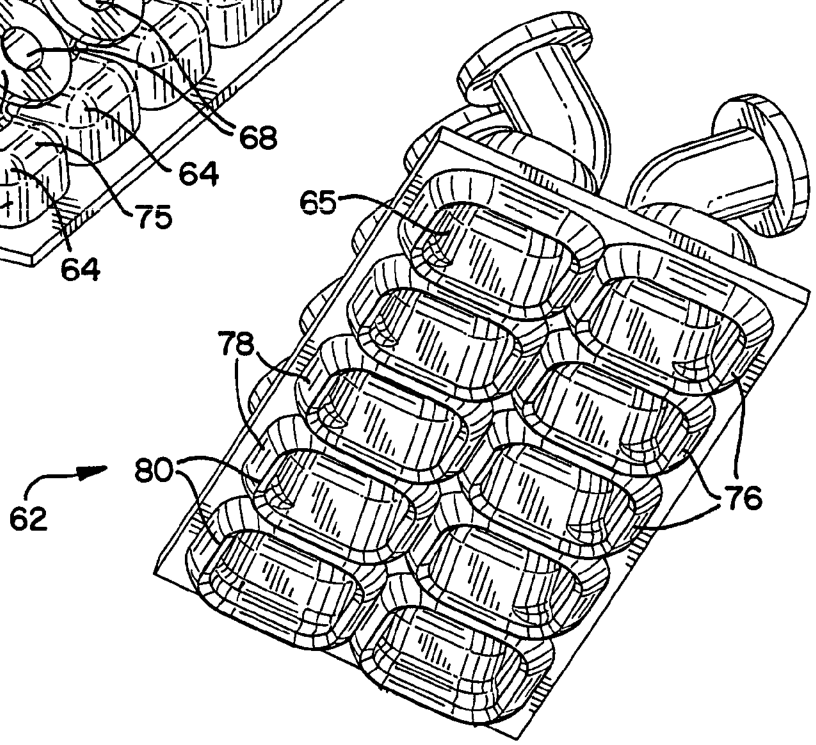
FIG. 3*b* is a bottom perspective view of a gasket.
Figure 3C:
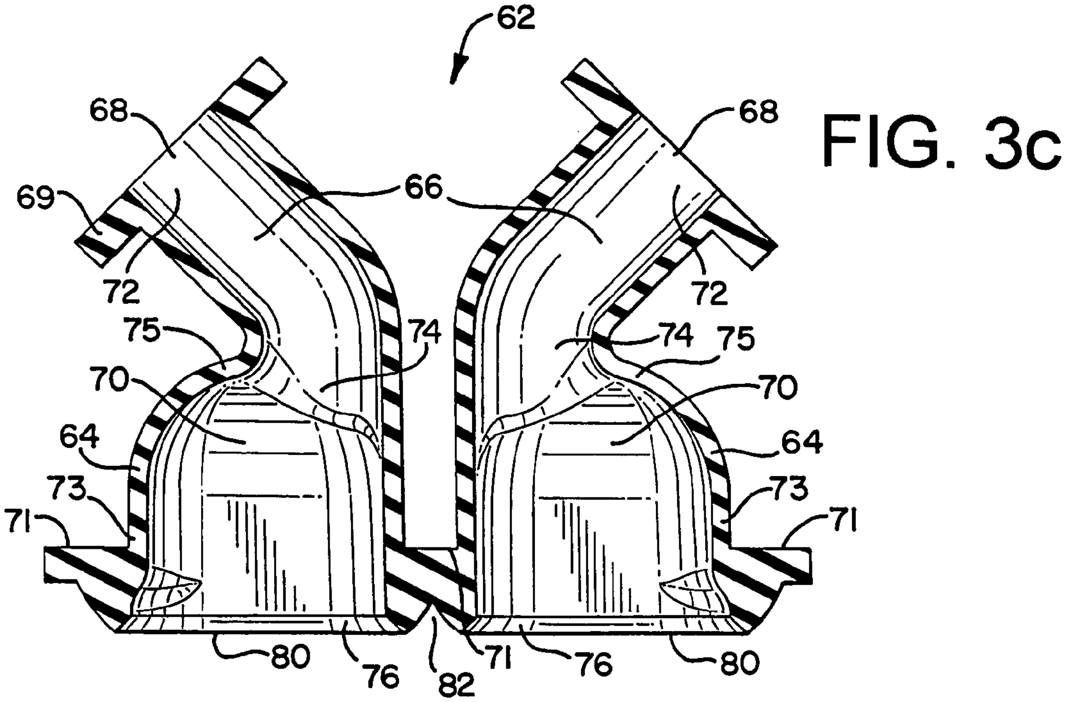
FIG. 3*c* is a cross-sectional view of a gasket.

Referring to FIGS. 3*a*–3*c*, there are shown a top and bottom perspective view and a cross-sectional view of gasket 62. Gasket 62 may be at least partially composed (and in one embodiment entirely composed) of pliable material such as a natural or synthetic elastomer and may be used to form a seal with substrate 20. Specifically, the contact point of the gasket 62 to the substrate 20 may be pliable such that a seal is formed. Gasket 62 may include a plurality of sections, each of the sections may include sidewalls 64, a neck portion 66 and at least one opening 68. FIGS. 3*a*–3*b* shows gasket 62 with ten sections, so that a total of ten hybridization chambers for each of the areas 22 may be created.

Sidewalls 64 may, for example, comprise four sidewalls which are perpendicular to the area 24 (which is square in shape) on substrate 20. Further, sidewalls 64 may be curved where the sidewalls meet 65 so that liquid is not trapped at the sections where the sidewalls abut. Alternatively, the sidewalls may be continuously curved.

Figure 14C:
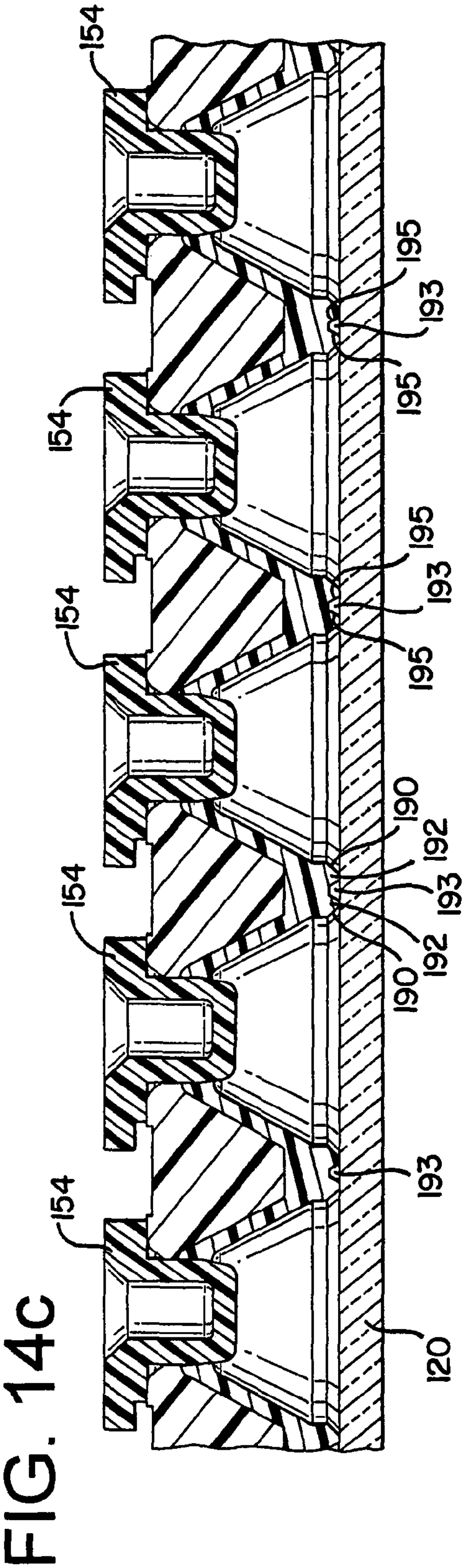
FIG. 14*c* is a cross-sectional view of a substrate, and a plurality of hybridization chambers, substrate, openings and protrusions.
Figures 15A, 15B, 15C:
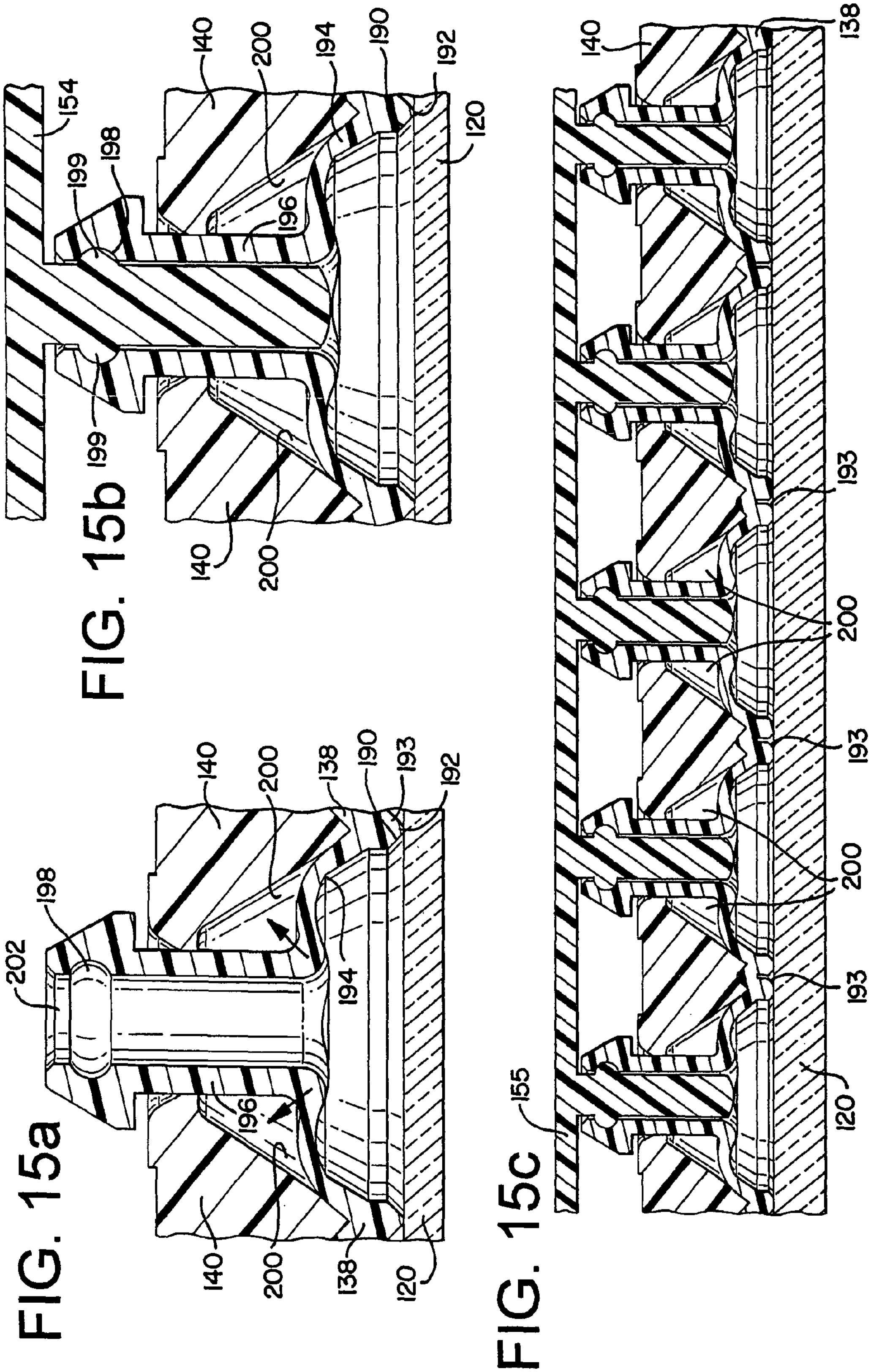
FIG. 15*a* is a cross-sectional view of a substrate, another embodiment of a hybridization chamber, and opening.
FIG. 15*b* is a cross-sectional view of a substrate, another embodiment of a hybridization chamber, opening and protrusion.
FIG. 15*c* is a cross-sectional view of a substrate, and a plurality of hybridization chambers, substrate, openings and protrusions.

The plurality of sections may further include a neck portion 66, as shown in FIG. 3*c*. Neck portion 66 provides a conduit from opening 68 to the inner portion 70 bounded by substrate 20 and sidewalls 64. Specifically, the neck portion 66 has a first end 72 which is connected to opening 68 and a second end 74 which is connected to the inner portion 70. The neck portion 66 may be angled (either a sharp angle or a curved angle), as shown in FIG. 3*c* or straight, as shown in FIGS. 15*a*–*c*. Alternatively, the neck portion need not be included, as shown in FIGS. 14*a*–*c*. The angle of neck portion may be 180° (as shown in FIGS. 15*a*–*c*). Alternatively the angle of neck portion 66 may be less than 180°. The angle may be measured with one vector being perpendicular to the substrate 20 and the other vector being co-axial with neck portion 66. In one embodiment, the angle may be between 90° and 180°, as shown in FIG. 3*c*. Further, the connection point of the second end 74 of the neck portion 66 to the inner portion 70 may vary. For example, the second end 74 of the neck portion 66 may be centered above the geometric center of the area 22 enclosed within the sidewalls (as shown in FIGS. 15*a*–*c*). Alternatively, the second end 74 of the neck portion 66 may be centered at a point which is not directly above the geometric center of the area 22 enclosed within the sidewalls (as shown in FIG. 3*c*). Adjacent to the openings 68 may include an opening lip 69. Lip 69 may be adjacent to the entire opening 68, as shown in FIG. 3*a*. Alternatively, lip 69 may be adjacent to only a portion of opening 68. As described subsequently, lip 69 engages with cover 86 to provide a backing for openings 68. Further, gasket 62 may include a ledge 71. As described subsequently, a portion (or all) of ledge 71 may be used to abut a rigid material, such as beams 90 of cover 86. Cover 86 may thus be attached to either the substrate 20 or substrate holder 30, in order to apply pressure to gasket 62 to seal to substrate 20.

The height of the sidewalls 64 may vary. As shown in FIG. 3*b*, the height of the sidewalls 64 is on the order of the width of the area 22. This may reduce the surface tension around the interface of the area 22 and the sidewalls 64, allowing for more fluid inserted into inner portion 70 to be more evenly distributed on the surface of area 22. Alternatively, as discussed in more detail below, the height of the sidewalls 64 may be much less than the width of area 22, as shown in FIGS. 15*a*–*c*. Further, sidewalls 64 may be curved. As shown in FIG. 3*c*, sidewalls 64 may include a vertical portion 73, which is perpendicular to the substrate 20, and may further include a domed portion 75, which is curved and is not perpendicular to the substrate. The domed portion 75 may curve to the point where the sidewall is parallel (or approaching parallel as shown in FIG. 3*c* to the substrate 20.

In another aspect, the contact area of the gasket 62 and the substrate 20 reduce leakage out of the chamber. To reduce leakage, gasket 62 may include a compression rib 76, as shown in FIGS. 3*b* and 3*c*. The compression rib 76 contacts the substrate 20 to form a seal around a circumference of area 22. Compression rib 76 may be a shaped surface. For example, compression rib 76 may include an angled part 78 coming to a bottommost part 80. The bottommost part 80 may be in the form of a pointed tip, a rounded edge or a flat surface. The bottommost part 80 deforms when pressed against the substrate, thereby forming a seal. Further, an airspace 82 may be in between the bottommost part 80 between hybridization chambers, as shown in FIG. 3*c*. This airspace 82 may be formed by curved portions. Airspace 82 reduces the possibility of cross-contamination. If liquid leaks from a hybridization chamber, it may be trapped in airspace 82 and not travel to an adjacent hybridization chamber, thereby avoiding cross-contamination.

Figure 9A:
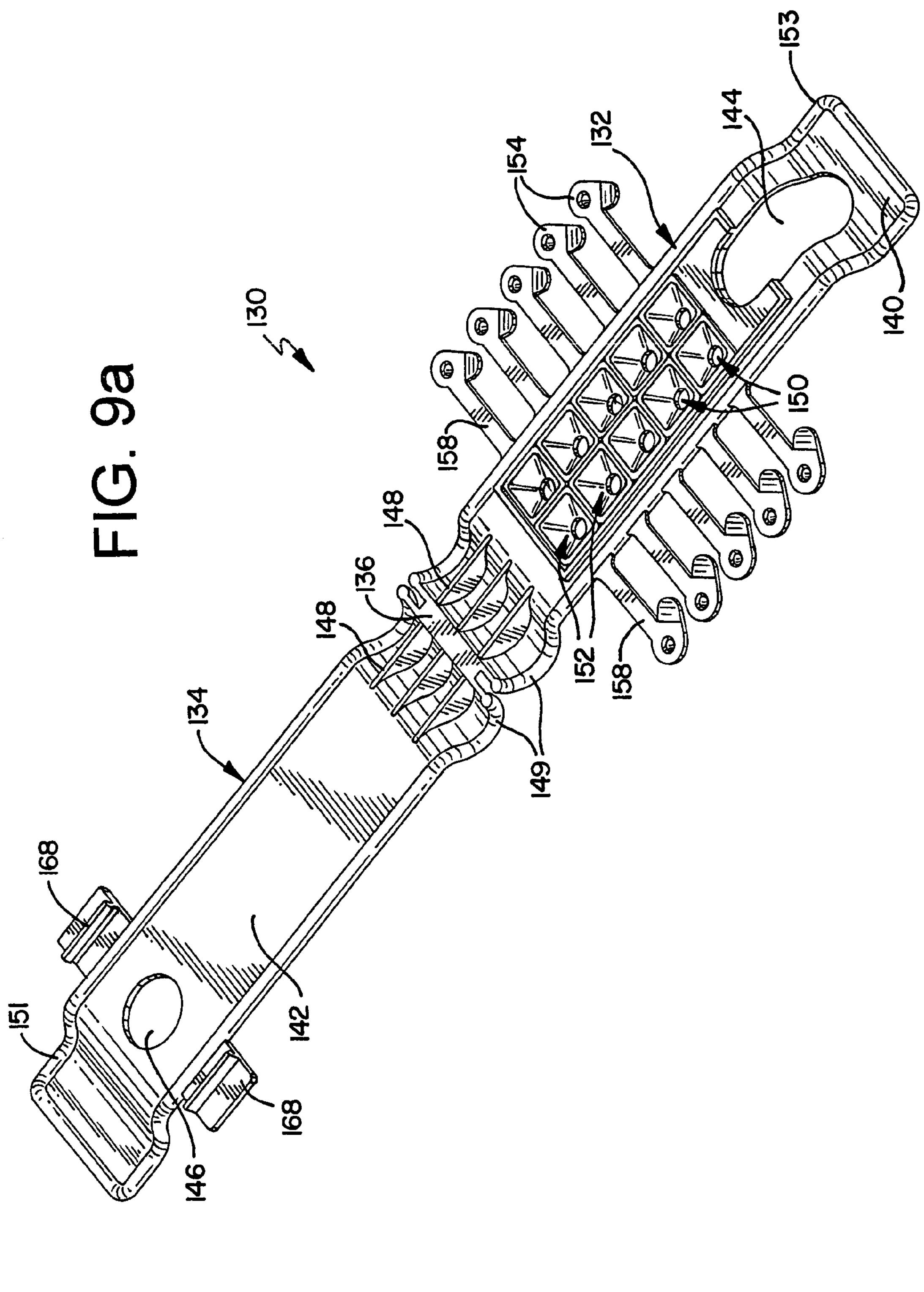
FIG. 9*a* is a perspective view of one embodiment of one side of the hybridization device.
Figure 9B:
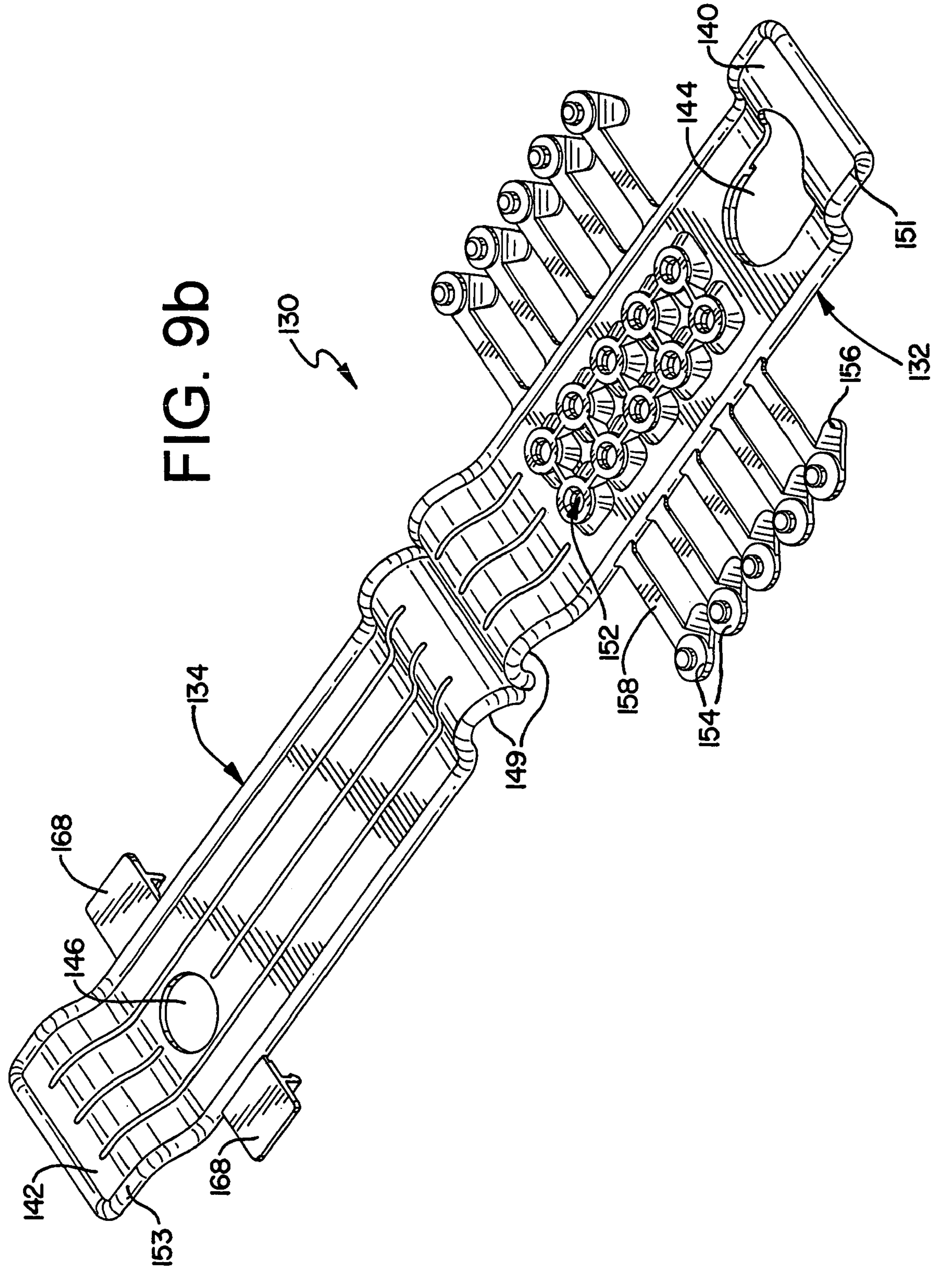
FIG. 9*b* is a perspective view of the opposite side of the hybridization device as shown in FIG. 9*a*.

As discussed above, a rigid material may be used in combination with the at least partly pliable material (such as the gasket 62). One example of the rigid material is shown in FIGS. 4*a* and 4*b* as top and bottom perspective views of one embodiment of a cover 86. As discussed subsequently, another embodiment of the rigid material is shown, for example, in FIG. 9*a*, as 140. As discussed above, cover 86 may be connected, either permanently or temporarily to substrate 20 or to substrate holder 30 (which holds substrate 20). This connection may allow the cover 86 to apply pressure to gasket 62 to form a seal with substrate 20. To apply pressure to gasket 62 to form a seal, cover 86 may be temporarily connected to substrate holder 30. One manner of temporary connection is via slots 88 on the cover 86. The slots 88 may engage reinforcing strips 42 of substrate holder 30. Other manners of connection of the cover 86 to the substrate holder 30 include clamps. Alternatively, the substrate holder may be more permanently connected to the substrate holder 30, such as by connecting the two pieces via a hinge, such as shown in FIG. 9*a* and 9*b*.

The cover 86 provides a rigid structure for gasket 62. Cover 86 may be composed of any rigid material, such as polycarbonate. As shown in more detail in FIGS. 6*a* and 6*b*, gasket 62 fits within cover 86. Cover 86 includes beams 90, which run down and across the cover, as shown in FIG. 4*b*. The beams 90 abut a portion of gasket (such as ledge 71) to apply a rigid backing to the compression rib 76. Therefore, when cover 86 engages substrate holder via slots 88, the beams 90 press compression rib 76 against substrate 20. Cover 86 further provides structure for opening 68. Opening 68 may include an opening lip 69. Cover 86 may include curved rigid portions 92 which abut the opening lip 69, providing a rigid backing for opening lip 69. As shown in FIG. 4*a*, curved rigid portion 92 is semi-circular, providing rigid backing for only a part of opening lip 69. Face seal assembly 98 may provide additional rigid backing for opening lip 69, as discussed subsequently. Alternatively, cover 86 may provide backing for all or nearly all of opening lip 69.

Cover 86 further includes openings 94. Openings 94 allow the engaging of the face seal assembly, as discussed subsequently with respect to FIG. 5. Further, openings 94 allow for air flow, promoting more even heating of the substrate 20 when engaged in the hybridization device. As shown in FIG. 4*a*, cover 86 may have a domed top. Alternatively, the rigid material may have a flatter configuration, as shown in FIG. 9*a*.

As discussed above, sealing of the openings 68 may be accomplished by inserting a protrusion into the opening, such as a cap. One example of this is shown in FIG. 5, which is a perspective view of a face seal assembly, used in combination with the cover of FIG. 4*a*, for sealing the openings 68 in the gasket 62. The face seal assembly includes a plurality of caps 100, each of which has a protrusion 102 for insertion into opening 68. The caps 100 include a tab 104 for ease of use. Further, caps 100 may be connected to the cover 86 via a retaining clip 106. The caps may operate on a hinge 107 to be inserted into and removed from openings 68. The retaining clip 106 may be inserted into cover 86, as shown in FIG. 6*a*. The retaining clip 106 may include structure for supporting the openings 68 of the gasket 62. As merely one example, the retaining clip may include a curved portion 108 to support an underside of the openings 68.

An alternate method of inserting protrusions into the openings is shown in FIGS. 7*a* and 7*b*, which are an exploded view and a perspective view of strip caps 110, with the cover of FIG. 4*a*. The stripcaps may include a plurality of protrusions 112 and may be hinged 114 to the cover 86 at one end. In operation, a tab 116 on the stripcaps 110 is pushed downward to insert the protrusions 112 into openings 68. The strip caps may be injection molded polycarbonate or a similar high strength plastic. As shown in FIG. 7*a*, a series of caps on one side of the hybridization device may be opened and closed simultaneously. Alternatively, caps may be individually opened or closed.

Figure 8A:
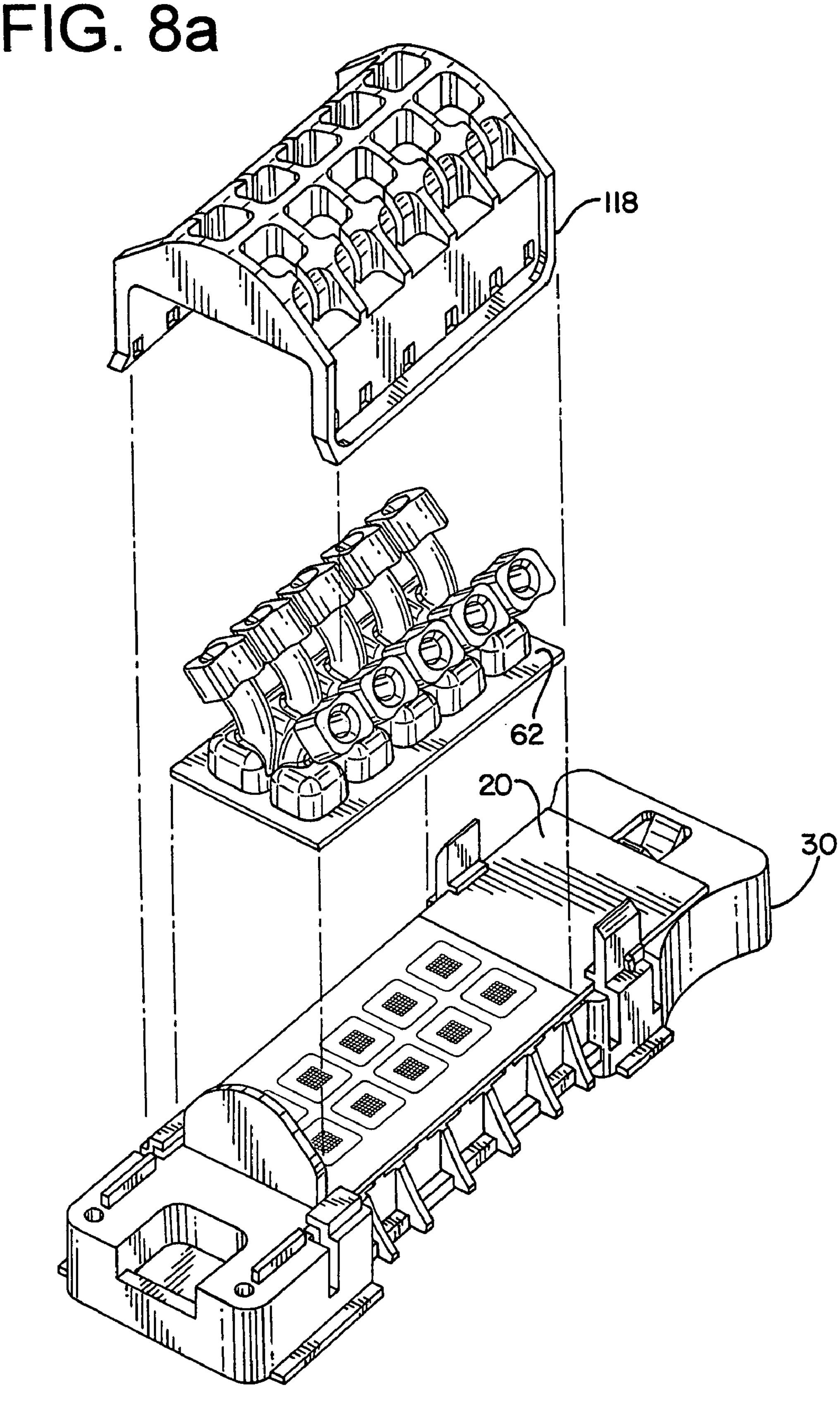
FIG. 8*a* is an exploded view of the substrate and substrate holder, gasket, and cover of FIG. 4*b*.
Figure 8B:
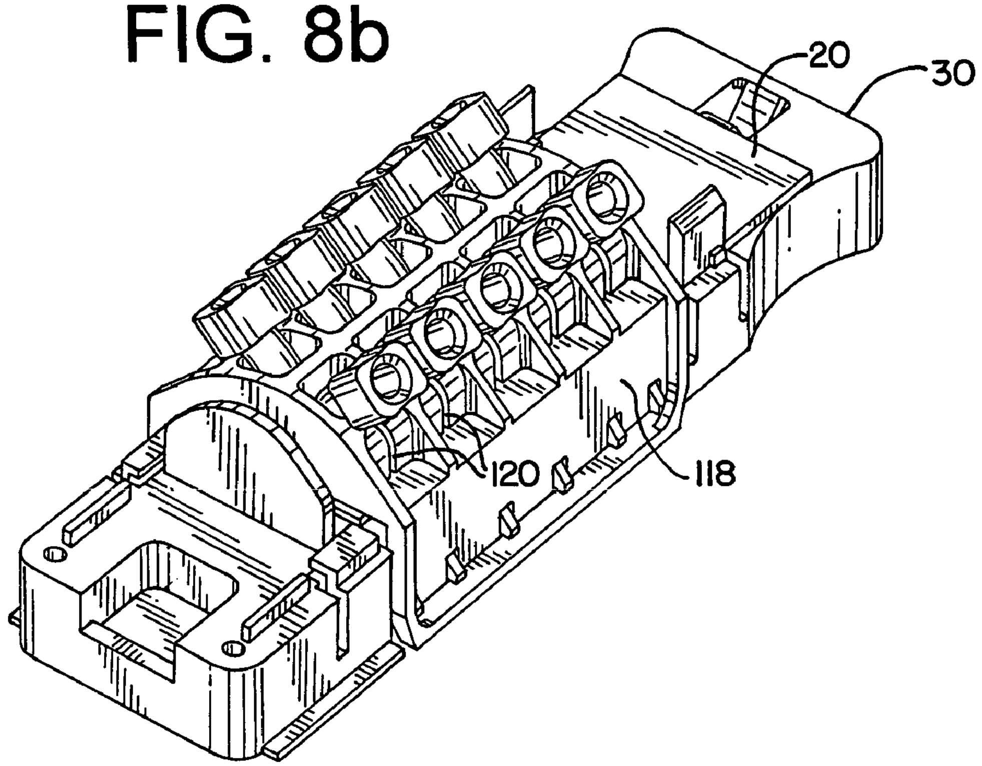
FIG. 8*b* is a perspective view of the substrate and substrate holder, gasket, and cover of FIG. 4*b*.
Figure 8C:
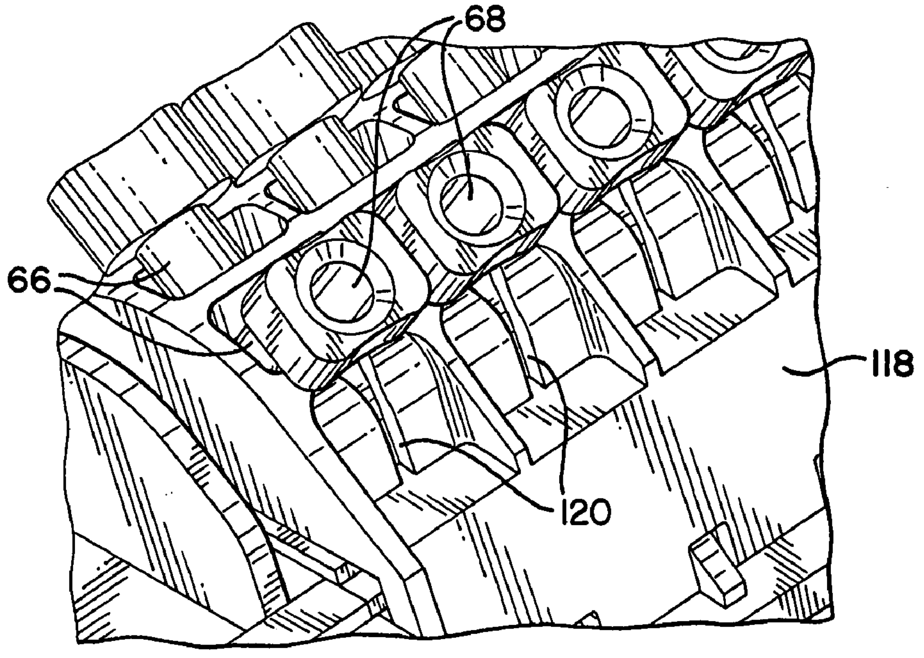
FIG. 8*c* is a perspective view of the gasket and cover of FIG. 4*b*.

Still an alternate method of sealing the openings is shown in FIGS. 8*a*–*c*, which are exploded view and perspective views of another embodiment of a cover which includes a sealing mechanism. Cover 118 operates similarly to cover 86 except for the sealing mechanism. As discussed above with respect to FIGS. 5 and 7*b*, cover 86 may work in conjunction with an additional device, such as separate caps to seal the openings 68. Cover 118 includes an integral sealing mechanism. The sealing mechanism includes grooves in the form of a v-groove 120 through which the neck portion 66 may be inserted. The v-groove 120 acts to pinch the neck portion 66, thereby sealing the opening 68. As shown in FIG. 8*c*, the openings 68 may be individually sealed by inserting neck portion 66 into v-groove 120.

Referring to FIG. 6*a*, there is shown a perspective view of the substrate, substrate holder, gasket and cover of FIG. 4*a*, and face seal assembly. The substrate 20 is engaged by substrate holder 30, using the substrate retention snap 45. As shown in FIG. 6*a*, the substrate 20 is slotted into the uppermost tooth 49 of substrate retention snap 47. In addition, substrate 20 is held by flexible bracket 46 and bracket 38. Further cover 86 is engaged in substrate holder 30 via reinforcing strips 42. FIG. 6*a* further shows a cap 100 which seals opening 68.

FIG. 6*b* is a side cross-sectional view of the substrate, substrate holder, gasket and cover of FIG. 4*a*, and face seal assembly. FIG. 6*c* shows a cross-sectional view of the substrate, substrate holder, gasket and cover of FIG. 4*a*, and face seal assembly. Further, FIG. 6*b* shows an end portion of a micropipette 122. Micropipettes, or other such devices, to introduce fluids into inner portion 70. This is shown, for example, in FIG. 18*b*. However, when introducing fluids into the chambers, care should be taken to avoid contaminating areas 22 on the substrate 20. The angle of neck portion 66 reduces the possibility that the tip of the micropipette 122 touches the areas 22 on the substrate 20, thereby avoiding contamination. Further, the placement of the second end 74 of the neck portion 66, centered at a point which is not directly above the geometric center of the area 22 enclosed within the sidewalls, further may reduce the possibility that the tip of the micropipette 122 touches the areas 22 on the substrate 20.

FIGS. 6*b* and 6*c* also show an air space 124 in between gasket 62 and cover 86. Leakage of fluid between hybridization chambers may be undesirable. Leakage may occur when pressure in the hybridization chamber builds up too high. Pressure may result due to high temperatures, for example, To reduce the pressure, an airspace or a gap 124 is formed between gasket 62 and cover 86, as shown in FIG. 6*b*. The gap 124 may be a fully enclosed or may be such that for at least a portion of the gasket 62, such as sidewall 64, the gasket 62 does not abut the cover 86. For example, a portion of the sidewall, such as the vertical portion 73, which is perpendicular to the substrate 20 and/or the domed portion 75 may have the gap 124 adjacent to it. In this manner, when pressure builds within the hybridization chamber, the pliable material of the gasket 62 (such as sidewall 64) may move outward, in the direction of the arrows, toward the rigid material of cover 86. Thus, the pliable gasket material may expand outward under pressure, reducing chances of leaking under high pressures.

Referring to FIGS. 7*a* and 7*b*, there are shown an exploded view and a perspective view of the substrate and substrate holder, gasket, cover of FIG. 4*a* and strip caps of FIG. 5*b*. During assembly, the gasket 62 may be inserted into cover 86. Thereafter, the combination of the gasket 62, cover (with sealing mechanism, such as the face seal assembly or strip caps), may be connected to the substrate holder 30 (which contains substrate 20).

Figure 10A:
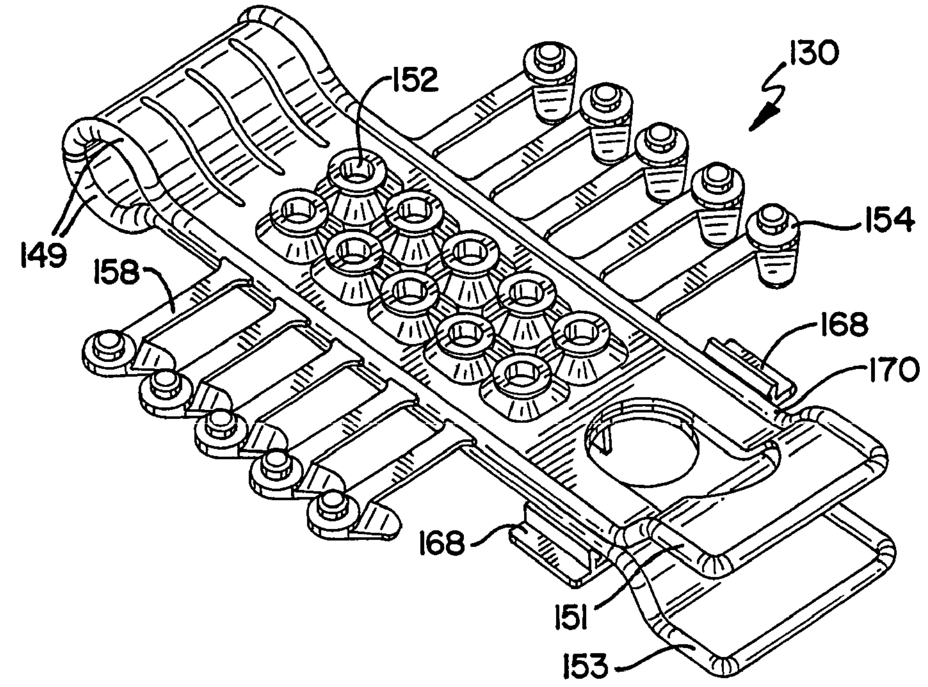
FIG. 10*a* is a perspective view of one embodiment of the hybridization device engaging a substrate, with the openings in the hybridization chambers unsealed.

Referring to FIGS. 9*a* and 9*b*, there are shown perspective views of an alternate embodiment of the hybridization device in the open position. The hybridization device 130 may include two main portions 132, 134, connected by a hinge 136. As discussed above, the two portions need not be connected by a hinge (with the substrate holder 30, the cover 86 and gasket 62 being connected via clamps or press-fit). The first portion 132 includes a pliable material 138 and a rigid material 140. Similar to gasket 62, pliable material 138 may be composed of a natural or synthetic elastomer and is used to form a seal with the substrate, as discussed in more detail subsequently. The rigid material 140 may be composed of a plastic material, such as nylons (either glass or non-glass filled), polypropylenes or polycarbonates. The pliable material 138 may be press fit or over-molded into a portion of rigid material 140. Alternatively, the pliable material 138 may be glued to rigid material 140. The second portion 134 may include a rigid material 142. The rigid material 142 may be composed of the same material as rigid material 140, or may be composed of a different material. The first portion 132 and second portion 134 both may include holes 144, 146. When the hybridization device 130 is closed, as shown in FIG. 10*a*, the hybridization device may more easily be held using hole 144. Further, an edge of the substrate within hybridization device 130 may more easily be examined with holes 144, 146. For example, a bar code near an edge of substrate 20 may be read using a bar code reader to determine the probes bound to (he substrate or the tests to be performed. The first portion 132 and the second portion 134 may further include slats 148. The slats 148, upon closing of the hybridization device, provide added structure for rigidity of the hybridization device 130. The slats may be evenly space (as shown in FIG. 9*a*) or unevenly spaced. Further, the slats 148 may be on the first portion 132, the second portion 134, or both the first and second portions 132, 134 (as shown in FIG. 9*a*).

Figure 13:
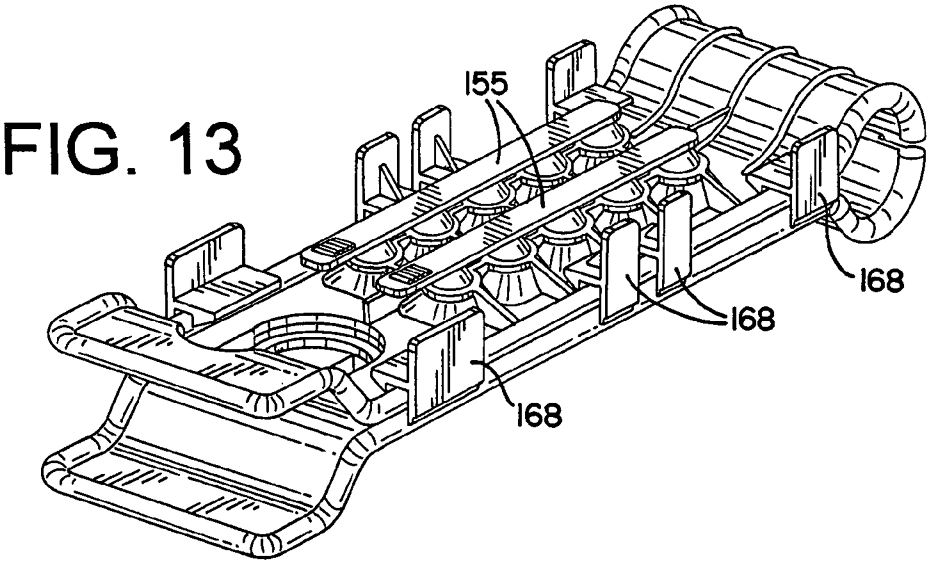
FIG. 13 is a perspective view of one embodiment of the hybridization device engaging a substrate, with all of the openings in the hybridization chambers sealed by caps with a common tab.

As shown in FIGS. 9*a* and 9*b*, the pliable material 138 includes openings 152. As discussed in more detail in FIGS. 14*a*–14*c* and 15*a*–15*c*, the hybridization chamber includes sidewall(s) 150 and an opening 152. Protrusions may be inserted into the openings 152, thereby sealing the opening. Thus, the opening and the pliable material/substrate interface are sealed, sealing the hybridization chambers. As discussed above, one example of a protrusion is a cap 154. The cap 154 may be designed to form a seal with the opening 152. The caps 154 may be composed of a pliable material, a rigid material or a combination of a pliable and rigid material. For example the caps 154 may be composed of the same material as rigid material 140. Alternatively, the caps may be composed of the same material as pliable material 138. The caps further may include a tab 156 attached to the cap. The tab 156 may be composed of a rigid material or a pliable material. Further, the cap 154 or the tab 156 may include identifying indicia, such as letter(s) or number(s). This identifying indicia may identify the particular experiment in the specific hybridization chamber and facilitate record keeping and tracking. The caps and tabs thus may allow for individual access to hybridization chambers. Alternatively, more than one cap, such as a row of caps as shown in FIG. 13, may be connected together using a common tab 155. The cap 154 may be attached to the main body of the hybridization device. For example, the cap 154 may be attached to the first portion 132 by a connecting portion 58. As discussed above, sealing may also be accomplished by compressing a rigid cover (such as a cover) over the pliable gasket.

The user may place the substrate face down onto the pliable material 138 so that the areas on the substrate are orientated towards the pliable side. When the hybridization device is closed with the clamps attached, as shown in FIG. 10*a*, the substrate and the pliable material abut one another. The substrate can be held within the hybridization device so that the hybridization chambers, including openings 152, are properly oriented in relation to the areas on the substrate. For example, in one embodiment, the openings 152 are oriented above the areas on the substrate. Thus, the position of the chambers is such that the areas may be centered below each opening 152. Proper placement of the substrate within hybridization device may be accomplished in several ways. As discussed above, springs (such as plastic springs) and/or brackets may be used. In another embodiment, guide pins 160 may be used to situate the substrate in the proper x and y position. For example, the guide pins 160 may be placed along each of the edges of the substrate, such as proximate to the corners of the substrate, to situate the substrate relative to the pliable material 138. Alternatively, the substrate may be guided using a raised wall, against which an edge of the substrate abuts. Specifically, the raised wall may be along one, two or more edges of the substrate. In still an alternate embodiment, slots may be used to guide the substrate. An edge or a corner of the substrate may be slid underneath the slots to properly orient the substrate.

As discussed above, the hybridization chambers are formed by abutting a pliable material with the substrate to form a seal with a portion of at least one side of the substrate. For example, as shown in FIG. 10*a*, the user may close the hybridization device and snap it shut so that the hybridization device may sandwich the slide, with the slide holder abutting both sides of the slide in order to form the hybridization chambers. Alternatively, the hybridization device may abut only one side of the substrate.

Figure 12:
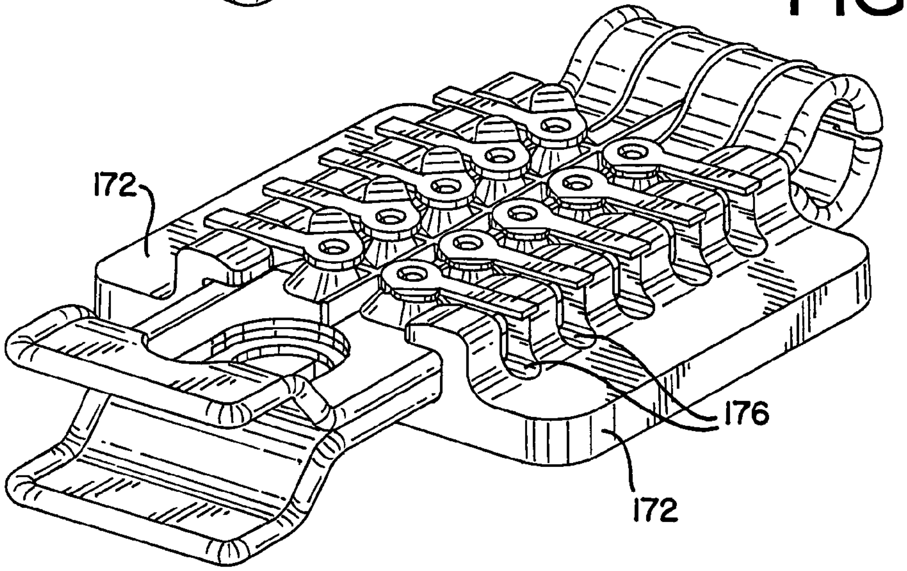
FIG. 12 is a perspective view of another embodiment of the hybridization device engaging a substrate, with a separate clamping device.
Figure 16:
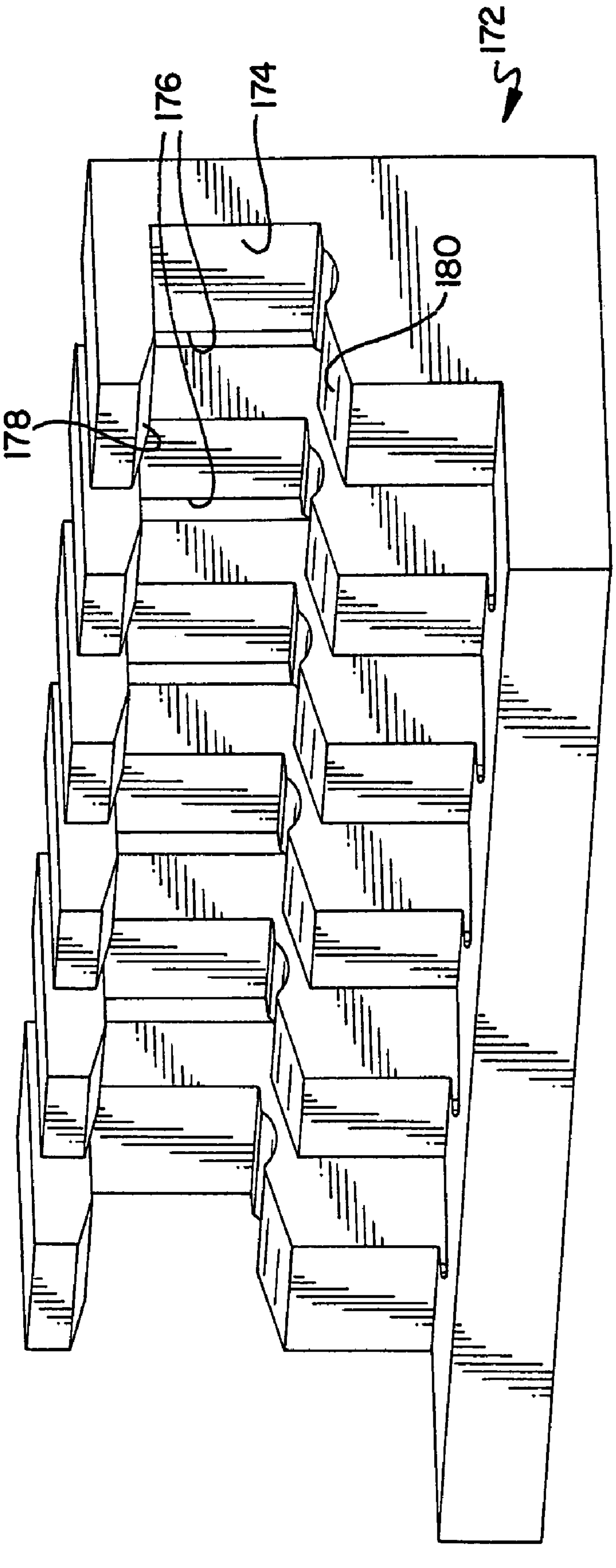
FIG. 16 is a perspective view of the clamping device as shown in FIG. 12.

One example of a manner to press the pliable material is using a clamp, clip or the like. A clamp or a series of clamps may connect the rigid portions together, thereby pressing the pliable material against the substrate. As shown in FIG. 10*a*, the first portion 132 is connected to and integral with the second portion 134 by a clamp 168. As shown in FIGS. 9*a*–9*c*, the clamps 168 are connected to the second portion 134. When closing the hybridization device 130, the clamps 168 are snapped onto the first portion by clearing a lip 170. Alternatively, the clamp may be connected to the first portion 132 and snap onto the second portion 134. In still an alternate embodiment, the clamp is not integral with either the first or second portions 132, 134. Instead, the clamp is a separate piece which connects the first and second portions 132, 134. One example of such a clamp is shown in FIGS. 12 and 16. The clamp 172 includes a back wall 174, against which the edges of the first and second portions 132, 134 may abut. Further, the clamp 172 includes breaks 176. The breaks 176 allow for connecting portion 158 to be integrated with clamp 172, as shown in FIG. 12. Clamp 172 further includes slanted portions 178, 180. The slanted portions 178, 180 allow for the clamp 172 to be snapped into place. As shown in FIG. 12, two clamps are used along opposite edges of the first and second portions 132, 134. Alternatively, only one clamp along one edge may be used. Further, as shown in FIG. 12, one clamp 172 is along a part of an edge of the first and second portions 132, 134. Alternatively, a series of separate clamps may be along a part of the edge of the first and second portions 132, 134. In an alternate embodiment, the pressing of the pliable material may be accomplished by using an adhesive. The adhesive may be applied to the portion of the pliable material 38 abutting the substrate. As discussed above, the clamp may be made a part of the top or bottom part of the gasket, and snap into slots in the alternate piece.

When the hybridization device is closed, curved portions 149 at one end and curved portions 151 and 153 enable easy holding of the hybridization device. For example, the closed hybridization device may be held between the thumb and finger at curved portions 149. Alternatively, the closed hybridization device may be held between the thumb and finger at curved portions 151 and 153. Further, the curved portions 149, 151 and 153 raise the main body of the hybridization device (the portion of the hybridization device between the curved portions) above the flat surface upon which the hybridization device sits, allowing for easier handling.

Figure 10B:
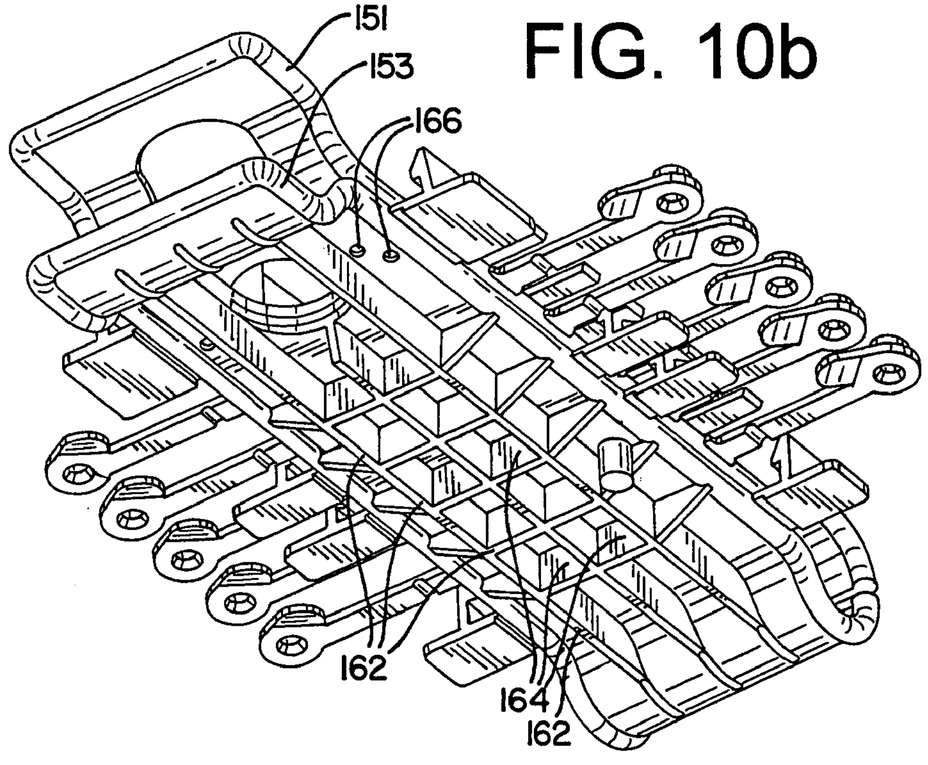
FIG. 10*b* is a perspective view of an alternate embodiment of the opposite side of the hybridization device engaging a substrate, with the openings of in the hybridization chambers unsealed.
Figure 11:
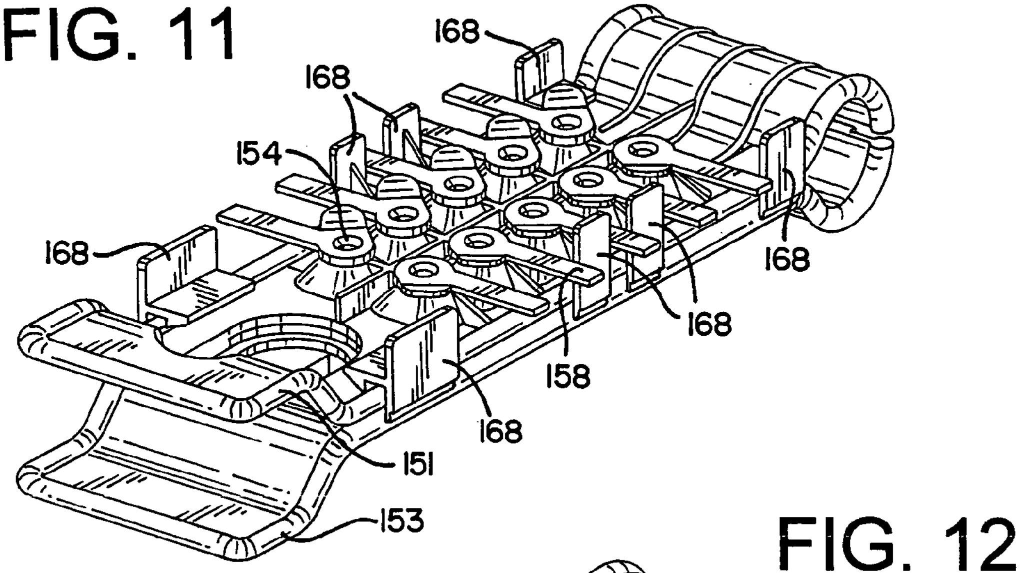
FIG. 11 is a perspective view of one embodiment of the hybridization device engaging a substrate, with some of the openings in the hybridization chambers sealed.

Referring to FIG. 10*b*, there is shown a perspective view of an alternate embodiment of the second portion 134 of the hybridization device. The second portion 134 may include slats 162 running both along and across the second portion. The slats 162 add stiffness to the second portion 134. Further, the slats 162 form pockets 164 on the second portion, which allow for air to be trapped therein. The air allows for the hybridization device to be buoyant when placed in a liquid bath, if that buoyancy of the hybridization device is sought. Further, as shown in FIG. 10*b*, the second portion 134 may include holes 166. The holes 166 allow for the guide pins to fit in when the first portion 132 is pressed flat against the second portion 134. Otherwise, the guide pins, which are raised, may break.

In another embodiment, the hybridization chambers are designed to be fully enclosed. An enclosed hybridization chamber allows for easier mixing of the specimen. In particular, rather than requiring a separate vortex mixing device (as discussed subsequently in FIG. 17), mixing may be performed manually. The hybridization chamber can also be placed on a vortex mixing device for mixing. Further, the enclosed hybridization chamber reduces the possibility that liquids may evaporate or leak from the hybridization chamber. In one aspect, the hybridization chambers are designed with access caps so that the access cap may seal the opening in the hybridization chamber. This is shown in the cross-sectional view of FIG. 14*b* of a substrate, a hybridization chamber, opening and cap. The rigid material 140 has an opening 184 for entry of the cap. Likewise, the pliable material has an opening 152. The opening 184 is tapered inward to allow for ease of entry of cap 154. The opening 152 also is tapered, with a slanted portion 186 and a vertical portion 188. Upon insertion of cap 154, as shown in FIG. 14*b*, the opening 184 maintains it shape. By contrast, the shape of opening 152 is modified, with the opening being pushed outward. This allows for a seal to be formed so that fluid will not leave the chamber from opening 152. In another aspect, the contact area of the pliable material 138 and the substrate reduce leakage out of the chamber. For example, as shown in FIG. 14*a*, the pliable material includes an angled portion 190 coming to a bottommost portion 192. The bottommost portion 192 may be in the form of a pointed tip, a rounded edge or a flat surface. As shown in FIG. 9*a*, the bottommost potion 192 forms a narrow edge around the circumference of the pliable material. This bottommost portion 192 deforms when pressed against the substrate, thereby forming a seal. Further, an airspace 193 is formed in between the bottommost portions 192 between hybridization chambers, as shown in FIG. 14*c*. This airspace 193 may be formed by curved portions 195. Airspace 193 reduces the possibility of cross-contamination. If liquid leaks from a hybridization chamber, it may be trapped in airspace 193 and not travel to an adjacent hybridization chamber, thereby avoiding cross-contamination.

In another embodiment, the hybridization chambers are in a form to minimize fluid on the sidewalls or top and maximize fluid on the slide. The hybridization chamber may be formed such that the surface area for the slide is larger than the surface area at the top of the chamber. For example, the hybridization chambers may be in the form of a dome with the top portion being used to insert fluids, such as reagents, and the bottom portion being for the slide portion. This is shown in the cross-sectional view in FIG. 14*a* of a substrate, a hybridization chamber, and opening. This is also shown in the cross-sectional view in FIG. 14*c* of a substrate, a plurality of hybridization chambers, openings, and caps. In this manner, when fluids are pipetted into the hybridization chamber, the fluids are less likely to concentrate on the walls and more likely to settle on the bottom portion of the hybridization chamber. This is in contrast to a hybridization chamber which has the same cross-section from the bottom to the top of the chamber. Fluids inserted at the top of such a hybridization chamber are less likely to settle all of the fluid on the bottom portion. As shown in FIG. 14*a*, sidewall 150 is angled such that the upper portion of the chamber is narrower than the lower portion which contacts the substrate. As shown in FIG. 9*a*, there are four flat sidewalls. Where the sidewalls meet, the intersection is curved to reduce the possibility that fluid may be trapped. The sidewall may alternatively be conically shaped sidewall.

Referring to FIGS. 15*a*–*c*, there is shown an alternate embodiment of the hybridization chamber. Reducing leakage of fluid from the hybridization chamber may be accomplished through design of the pliable material 138. Pliable material includes a lower curved portion 194 and an upper neck portion 196. The neck portion 196 may be cylindrical in shape. Further, a hole or air space 200 is formed between pliable material 138 and rigid material 140. In this manner, when pressure builds within the hybridization chamber, the pliable material may move outward, in the direction of the arrows, toward the rigid material. This movement outward of the pliable material reduces the pressure. FIG. 15*a* further shows pliable material 138 raised above rigid material 140. The raised part of the pliable material includes an opening 202. The opening includes an annular ring 198, which may engage a cap, as shown in FIGS. 15*b* and 15*c*. The cap may include a nub portion 199, which engages annular ring 198. Neck portion 196 may be wide enough so that fluid does not adhere to the surface of the neck portion 196. For example, the neck portion 196 may be 2.5 to 3 mm in diameter. Further, the upper part of neck portion may have a smaller diameter (e.g., 1.5 mm). In this manner, when a micropipette is used, the micropipette may be disallowed from full insertion into the hybridization chamber, thereby avoiding touching of the tip of the micropipette with the surface of the substrate. This may reduce the possibility of cross-contamination of the area on the substrate with the tip of the micropipette.

In addition, in one embodiment, the material can be chosen in order to maximize the amount of liquid on the slide. For example, at least a portion of the hybridization chamber may be made of a hydrophobic material. In one aspect, the sidewalls of the hybridization chamber are made with a hydrophobic material in order to repel liquid from the sidewalls so that the liquid may be placed on the microscope slide. In another aspect, both the sidewalls and the top of the hybridization chamber may be made of a hydrophobic material. The hydrophobic material may be of any kind which repels liquid. One example of a hydrophobic material is a thermoplastic elastomer. As discussed subsequently, portions of the device may be made of the thermoplastic elastomer (such as the sidewalls) while other portions, such as the access caps and structural support, may be made of another material, such as polypropylene or polycarbonate. Further, the material can be chosen in order to ensure a proper seal between the device and the bottom of the substrate. Since the hybridization device abuts the bottom of the substrate, a good seal should be maintained so that liquid in the chamber does not leak out. A material for the hybridization device which provides a good seal is silicone or a thermoplastic elastomer. Therefore, the portion of the device which contacts the slide (in one aspect the sidewalls) can be made of a rubber-based product or the like in order to form a sufficient seal between the slide and the device. The design should maintain its seals in its 10 individual chambers both at the cap and at the slide between −40° C. to 95° C. The chamber walls, which are rubber, are hydrophobic and will repel the reagent mixtures on to the slide surface. The volume of the chambers in FIGS. 14*a*–14*c* is approximately 200 microliters, which should help minimize the chance of the reagents not mixing thoroughly. Similarly, the volume of the chambers in FIGS. 15*a*–15*c* is approximately 100 microliters, which may help minimize the chance of the reagents not mixing thoroughly.

Processes Using Hybridization Device

After a substrate is placed within the hybridization device, such as the devices shown in FIGS. 6*a*, 7*b*, 8*b*, and 9*a*, the user may add the reagents for the first chamber and close the opening (such as by inserting the access cap). Closing the individual access caps after adding the reagents helps the user keep track of progress. Once the cap is closed, each chamber with its target is sealed. The substrate/hybridization device may then be placed in a thermally controlled environment, such as a water bath or dry oven, to execute the test. The DNA hybridization test can require two to three different temperatures and the design is intended to facilitate the movement of the slide holder into already controlled thermal environments to execute more rapid changes in temperature than if the environments temperatures had to change. The water bath allows for better control of the temperature than other heating devices, such as a surface heater. Specifically, a surface heater may heat portions of the slide unevenly, which may result in unreliable results. With the slide holder, a water bath may be used to control the temperature of the slide, thereby making the test more reliable.

Following hybridization, the user may open the access caps either individually or all in parallel in order to wash the non-hybridized DNA in solution out of the hybridization chamber. The wash could also occur in a water bath by the user inserting the slide holder and moving it back and forth to flush the unwanted solutions.

The DNA hybridization steps are now done and the target DNA, if it was present, is captured on the substrate's surface. In order to facilitate the measurements, a signal amplification step is sometimes performed. The slide holder's design, by being opaque and able to seal the slide's chambers, can facilitate the signal amplification process. To execute, the user would micropipette the signal amplification solutions into the hybridization chambers through the access port and close the access cap. The signal amplification solutions are now isolated from ambient light and can be brought to a specific temperature via insertion of the slide holder into a thermally controlled environment.

At the conclusion of the signal amplification steps the user would remove the slide holder from the thermally controlled environment, open the access caps, possibly add a stop solution via micropipette and then flush the solutions from the hybridization chambers with a wash process that might be similar to the DNA hybridization wash technique. The cover may be removed and the substrate in the substrate holder may be inserted into a device for measurement. In an alternate design, the slide holder can now be opened and the slide removed for measurements and archiving.

Referring to FIGS. 17*a–d*, there is shown a flow chart comparing a prior art process with the process using hybridization chambers. FIGS. 17*a–d* illustrate several aspects which increase the ease and reliability of the testing procedure. On one side is the discussion of the current process, as discussed above. On the other side is the discussion of the modified process of several aspects of the present invention. The modified process eliminates several steps in the conventional process and simplifies other steps. In the figure, an "X" denotes the elimination of a step, an "M" denotes a modification of a step and a "U" denotes an unchanged step. For example, as shown in FIG. 17*a*, the hybridization device removes the necessity of arranging the test tubes in a tube tray. Instead, the tubes are prearranged into a single preordered nest. Similarly, affixing of rubber gaskets to the substrate is eliminated. Referring to FIGS. 17*b–c*, the hybridization device, with the single nest concept, allows for the hybridization chambers to be mixed, heated and cooled together, rather than mixing, heating, cooling the individual test tubes. Similarly, with the separate hybridization chambers, washing the individual chambers reduces the possibility of cross-contamination of the chambers. By contrast, using an open rubber gasket, the substrate may become contaminated when washing, as shown in FIG. 10*d.*

Referring to FIGS. 18*a–f*, there is shown one example of a DNA diagnostic test which may be performed using the hybridization device. For efficiency, a plurality of hybridization units may be used. In the example shown in FIG. 18*a*, there are six hybridization units. More or fewer hybridization units may be used. The hybridization units may run a number of tests in a kit. If each hybridization unit has 10 wells, a total of sixty tests may be implemented. More or fewer wells may be designed in a hybridization unit. If 48 tests are desired, hybridization units with 8 wells may be used. Alternately, only 8 of the 10 wells of a 10 well hybridization unit may be used. In this example, the 6 hybridization units may be integrated with a 12 by 8 PCR tray with one hybridization unit for each column in a PCR tray. Further, in the present example, to integrate with standard multi-pipettes, the hybridization unit's wells may be 8.5 mm apart to be compatible with industry standard multi-pipettes.

Further, when performing PCR, PCR primers may be used with a sufficient material to run the tests. In the present example of 48 tests, 1 tube contains sufficient material. Hybridization probes are also necessary to run the tests, with 1 tube contains sufficient material to run 48 tests. Other consumable materials common to test/panels include: pure water; signal enhancement solution A & B; signal enhancement stop solution; wash solution; and hybridization buffer. Other materials may be used in tests.

In addition to consumables, equipment may be used in the diagnostic tests in this example: including: two water baths are used (one to denature at 95° C. and another to hybridize at 30 to 60° C.); a wash fountain; four wash baths; pipettes (s); centrifuge; and an imaging system (such as the imaging system disclosed in U.S. patent application Ser. No. 10/210,959 incorporated by reference in its entirety).

Figure 18A:
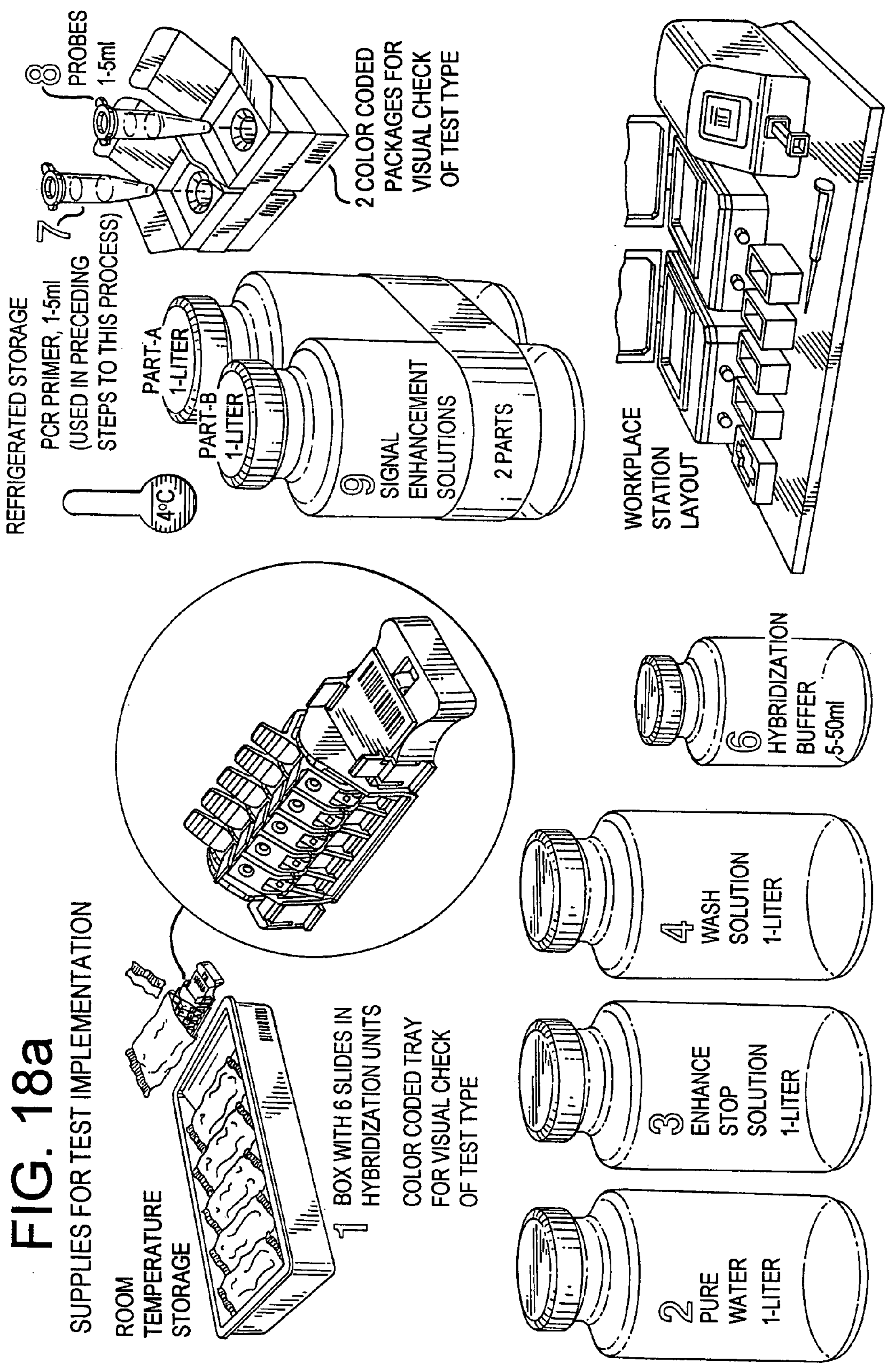
FIGS. 18*a–f* is a flow chart of one process using hybridization chambers.
Figure 18B:
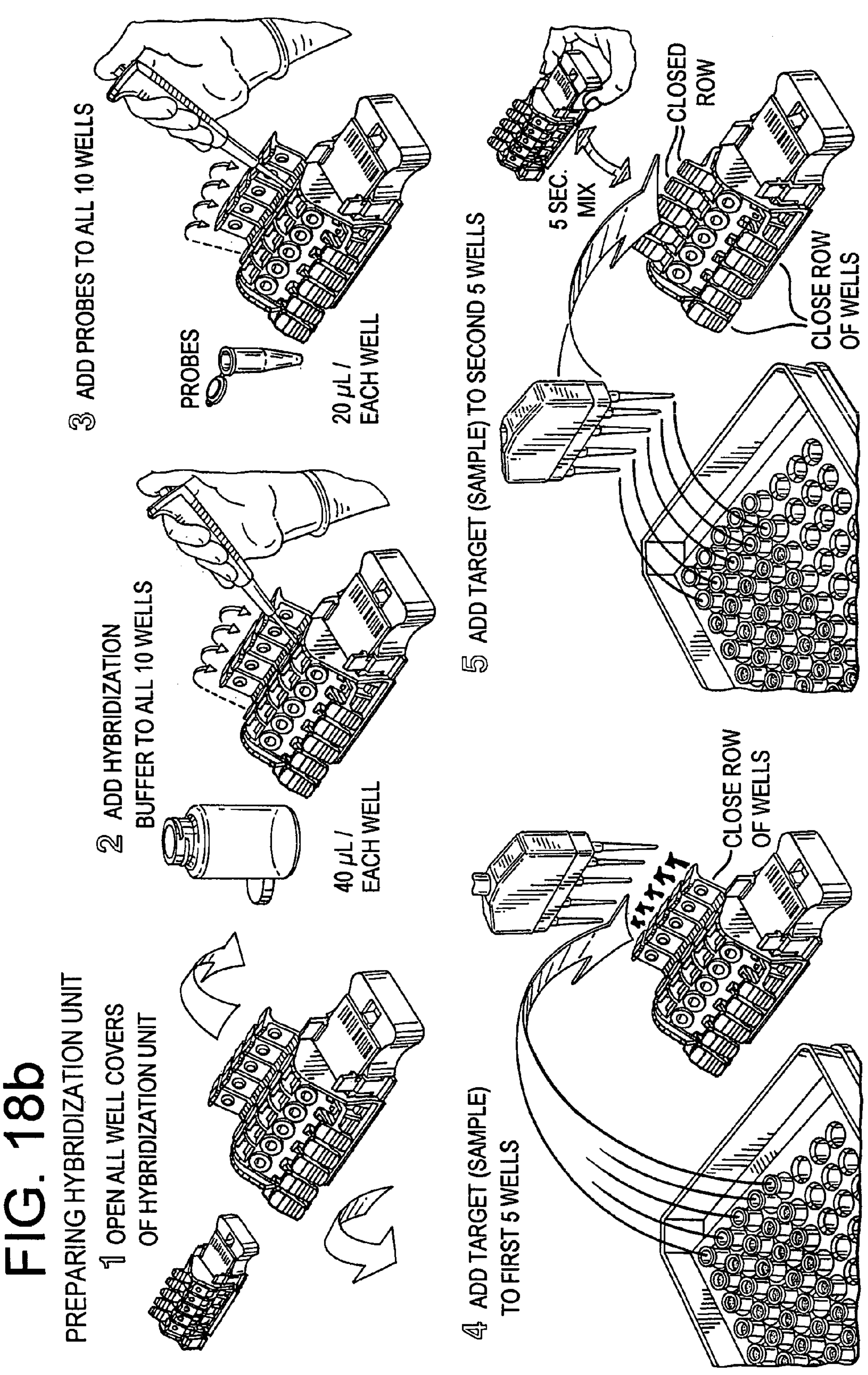
Figure 18C:
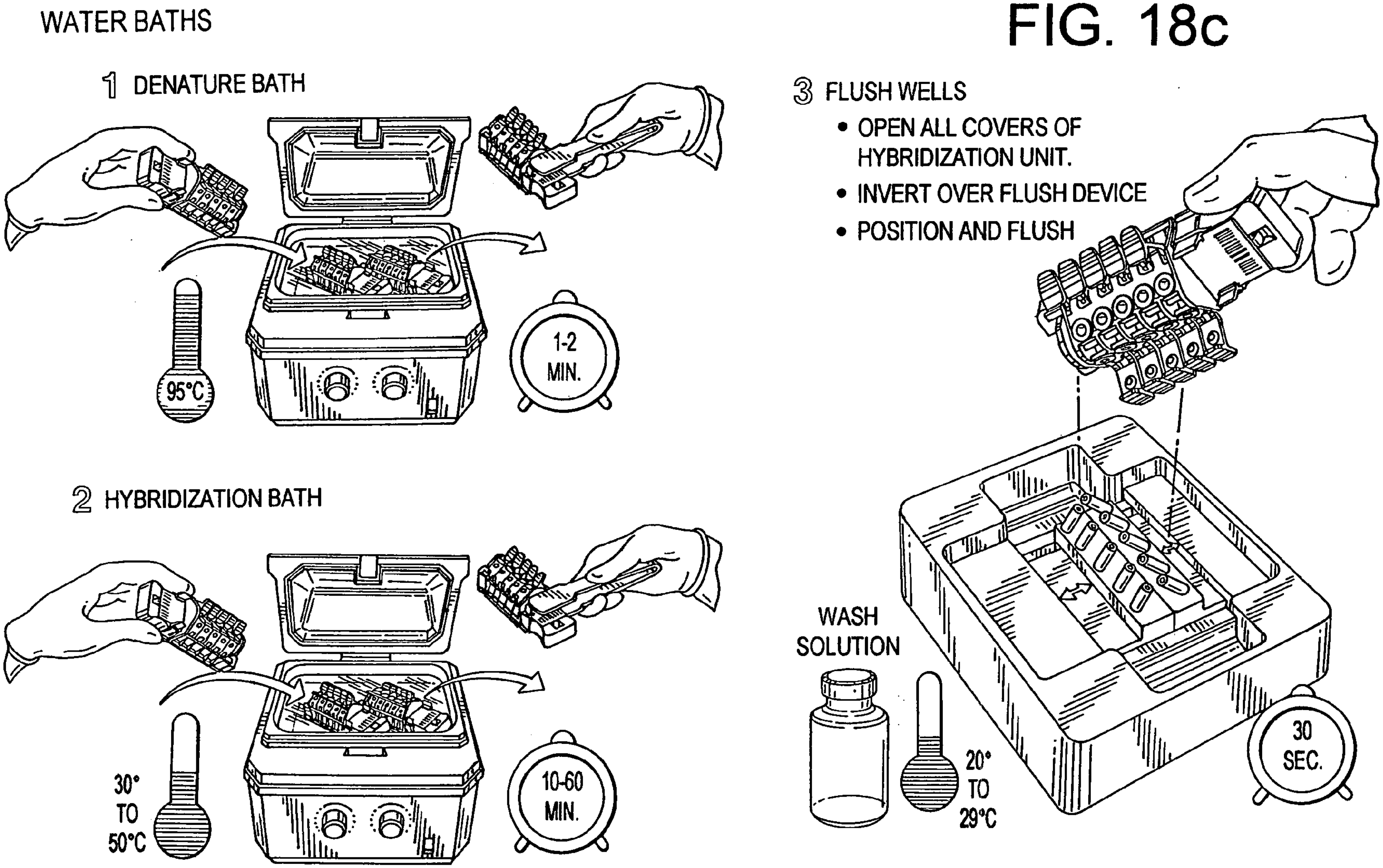

Referring to FIG. 18*b*, there is shown a sequence for preparing a hybridization unit. The imaging system, such as that disclosed in U.S. patent application Ser. No. 10/210,959, may print a worksheet for the user that will aid the user in recording the patient identification numbers and correlating them to a test slide and position on the test slide. The user may enter patient identification numbers and the PCR tray location when the user performs PCR on the DNA samples prior to the DNA diagnostic test. Alternatively, the patient id numbers/pcr tray location may be entered automatically, such as by using bar coding. The user may take a hybridization unit and mark a portion of the slide (such as the visible portion of the slide label) with a unique test identifier from the imaging system's worksheet that allows the user to track the patient identification information from the PCR tray location to the hybridization unit's well location and slide location.

As shown at block 1 of FIG. 18*b*, the user may open some or all of the well covers of the hybridization unit. As shown at block 2, the user may add hybridization buffer to some (or all) of the wells. For example, the user may add approximately 40 microliters of hybridization solution to each well. More or less hybridization solution may be used depending on the experiment performed and the size of the hybridization well. The hybridization solution may be colored to aid in spatial mapping and assist the user in identifying which wells have been loaded with probe solution. As shown at block 3, the user may then add probes to some (or all) of the wells. For example, the user may add approximately 20 microliters of probes to each well. The probe solution may be colored red, aiding the user in identifying which wells have been loaded with probe solution. As shown at blocks 4 and 5, the target (sample) may be added to the wells. Specifically, the patient's DNA samples may be transferred from the PCR tray to the hybridization unit. This transfer may be performed using a multi or single pipette. As shown in blocks 4 and 5, DNA sample is transferred to one side of the hybridization unit and the well's caps are closed. This minimizes the chance of double loading the well with two DNA samples. Further, closing the caps will help the user remain oriented at the proper well for DNA sample transfer. After closing the caps of the wells, the contents of the wells may be mixed by shaking the hybridization unit.

Referring to FIG. 18*c*, there is shown the sequence of using water baths in the present example. As shown in block 1, after loading the reagents into the hybridization wells, the user places the hybridization unit into the denature bath. The hybridization bath temperature is test/panel specific. Moreover, the time requirement and time tolerance for hybridization is test/panel specific. Typically, the denature bath is at 95° C. Further, typically after 1 to 2 minutes, the user moves the hybridization unit with tongs from the denature bath to the hybridization bath. As discussed previously, the hybridization unit contains pockets 64 to trap air. In this manner, the hybridization unit floats making handling easier. As shown at block 2, after removing the hybridization unit from the denature bath, the user places the hybridization unit into the hybridization bath. Typically, the hybridization bath is at 30 to 50° C. with the hybridization held in the bath for between 10 to 60 minutes. As shown at block 3, after removing the hybridization unit from the hybridization bath, the wells are flushed with wash solution. Specifically, the user opens the well's caps and places the unit on the wash fountain. The wash fountain may turn on when the hybridization unit is placed in the fountain causing the wash solution to be sprayed into the wells rinsing them of the DNA and the hybridization solution. The wash solution is typically at 20 to 25° C. and the flushing of the wells is performed for 30 seconds.

Figure 18D:
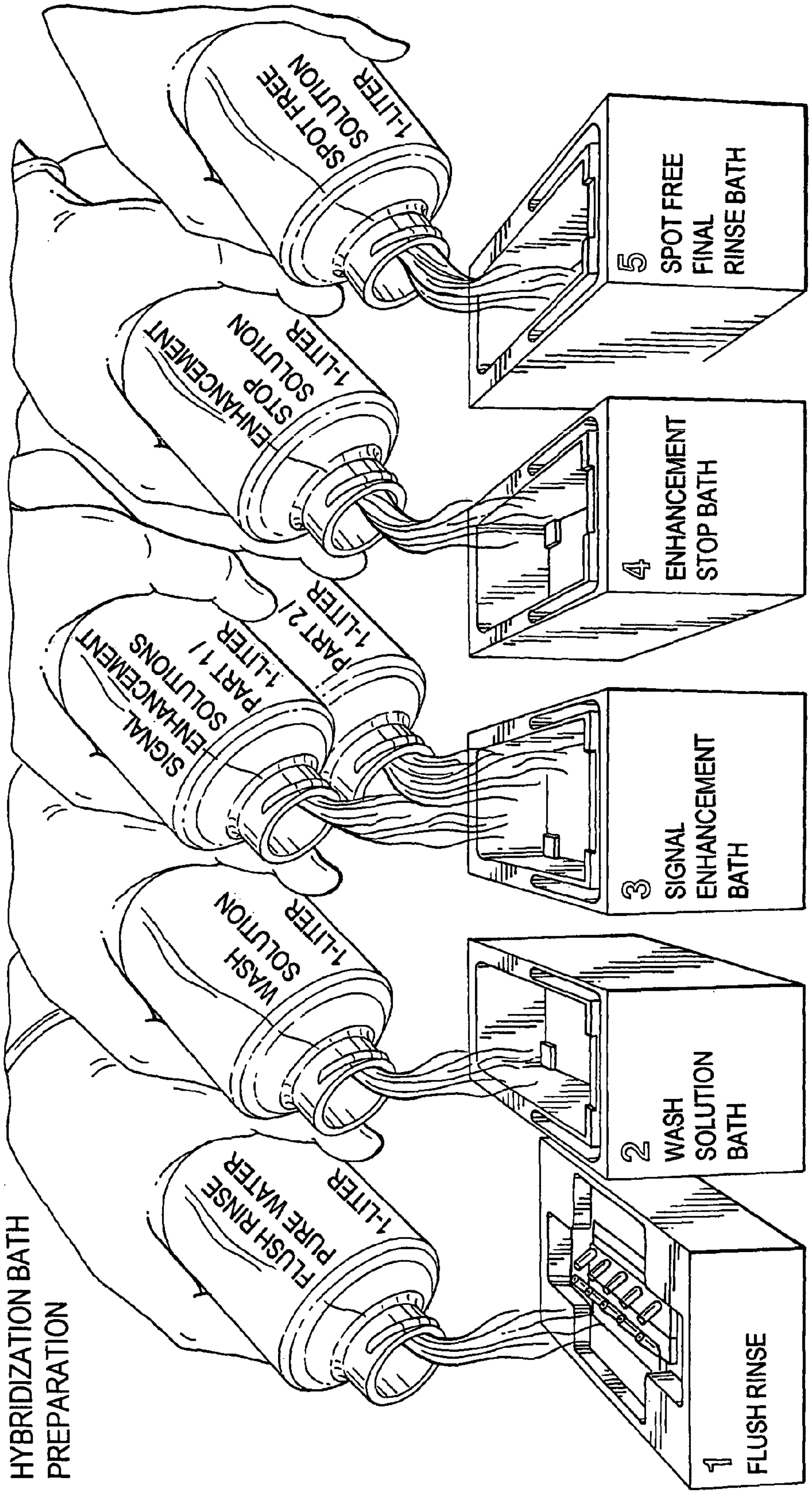
Figure 18E:
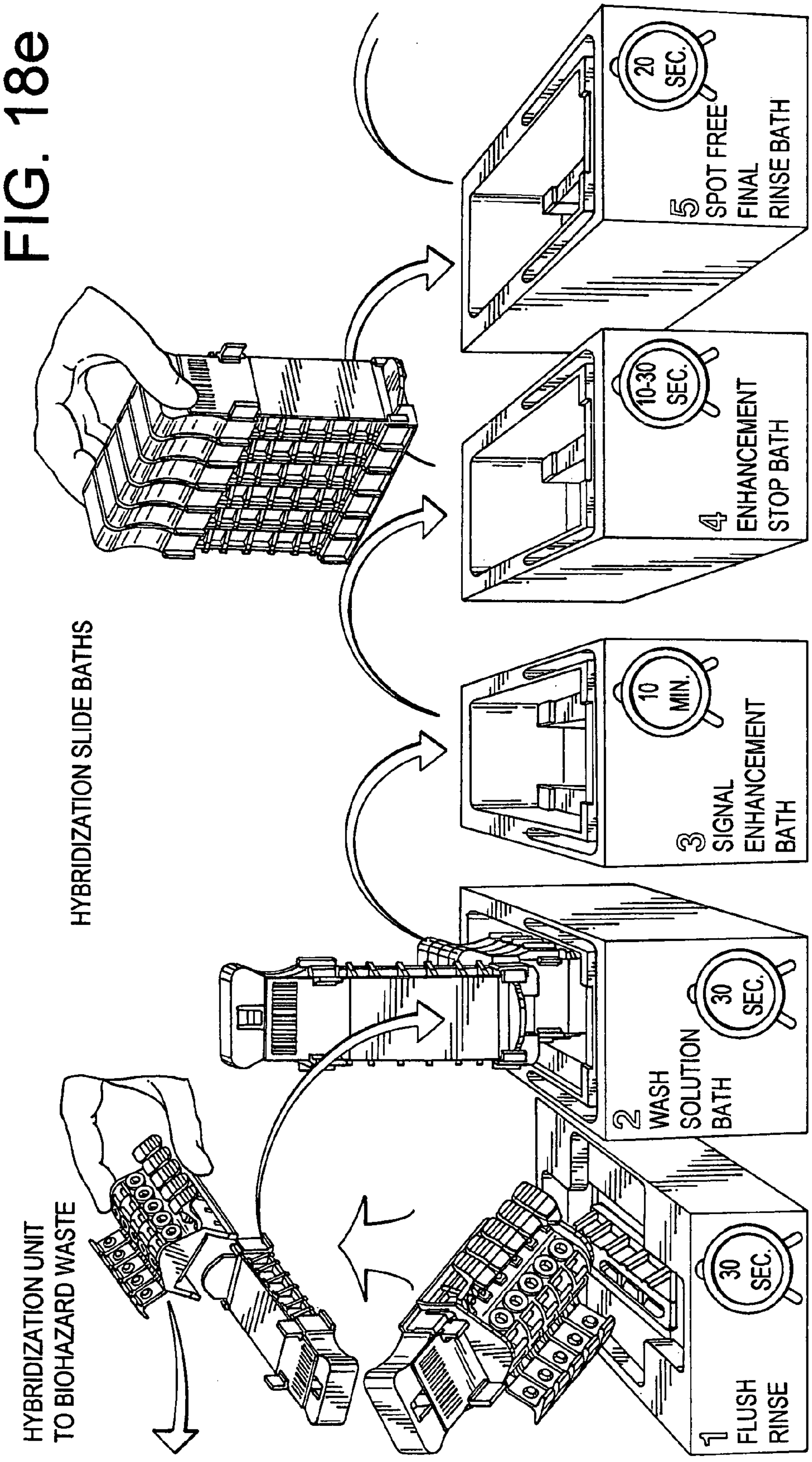
Figure 18F:
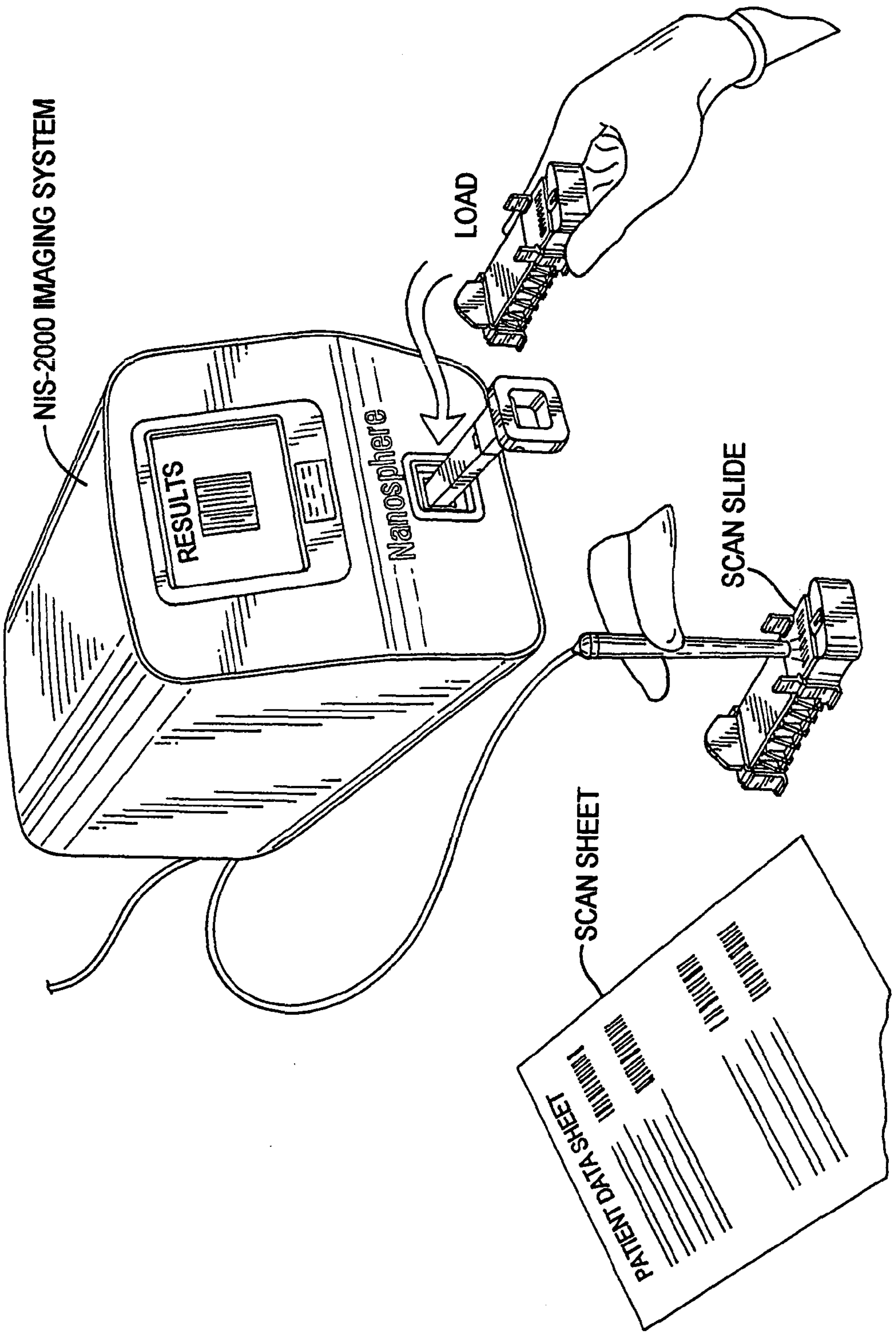

Referring to FIG. 18*d*, there is shown the hybridization bath preparation in the present example. The user may fill the wash fountain and the four wash baths with the appropriate solutions. For example, the wash fountain may contain wash solution. The wash solution bath may contain wash solution. The signal enhancement bath may contain signal enhancement solution. The enhancement stop bath may contain enhancement stop solution. And, the pure water bath may contain pure water solution. Typically, the signal enhancement solution is stored at 4° C. The wash solution, enhancement stop solution and pure water may be stored at room temperature. Further, the wash fountain and the wash baths may be designed to use 150 mL of solution. The wash fountain may process 1 slide at a time. Whereas, each wash bath may hold up to 6 slides at a time.

Referring to FIG. 18*e*, there is shown the hybridization slide baths in the present example. After the flush rinse using bath 1 in the wash fountain is complete, the user may open the hybridization unit and remove the substrate holder with the slide. The substrate holder (with slide) may be stacked on top of other substrate holders and immediately inserted into the carrier sitting in the filled wash solution bath 2. Alternatively, the slide may be removed from the substrate holder and processed either individually, or in combination with other slides using a carrier. The slide should remain in wash solution bath 2 for at least 30 seconds. However, the slide may sit in wash solution bath 2 for longer periods of time. The wash solution bath 2 acts as a collection buffer, collecting each slide until all slides in the test session, (e.g., up to a maximum of 6), are inserted into the slide carrier which is sitting in the wash solution bath 2. The user waits for at least 30 seconds once the last slide is placed into the carrier in the wash solution bath 2. The parallel processing of slides from this point (using baths 3, 4, and 5) may be from different tests.

The user may move the stack of substrate holders containing the slides from wash solution bath 2 to the signal enhancement bath 3. The carrier, with all the slides, may sit in the signal enhancement bath 3 for 10 minutes. The user may then move the carrier from signal enhancement bath 3 to enhancement stop bath 4. After 30 seconds, the user may move the carrier from the enhancement stop bath 4 to the pure water bath 5. The carrier may then be left in the pure water bath while the user removes one slide at a time and spins them dry, as shown in the following figure.

Thereafter, the slides may be dried. The slides may be loaded in the spin dryer. The slides may be spun dry for a certain period of time (e.g., 15 seconds). Referring to FIG. 18*f*, after finishing the spin dry, the slide's bar code may be scanned with the bar code wand which may obtain information regarding the slide including, but not limited to, inputting the test type and a unique serial number for record keeping. The imaging system may prompt the user to scan his/her bar code on his/her badge for record keeping. Further, the user may be instructed by the imaging system to load the slide and then be prompted to scan or enter in the patient identification for the DNA contents in well 1. The patient identification may be entered in a variety of ways. One method of input is via a bar code and bar code reader. Another method is via manual input using a numeric keypad on the imaging system. Scanning the patient id for well 1 may prompt the imaging system to feedback the information to the user with a beep and the scanned information on the screen. After an appropriate amount of time which allows the user to verify the proper scan, the imaging system may prompt the user to scan in the patient identification for the other wells on the slide (such as well 2, well 3, . . . and well 8). In parallel with the patient scan, the imaging system may automatically process the test results on the slide. So that, by the time the user completes the patient identification input, the imaging system may perform a slide scan and complete the analysis. The imaging system may provide a report (e.g., in printed format) for the user with the operator identification and patient identification correlated with the test results, test time, test date, the serial number, etc. In addition to a printed report (or instead of a printed report), the imaging system may provide an electronic report. The user may then place the slide into a standard slide box and remove the second slide from the carrier, sitting in the pure water bath, to spin dry and image.

Thus, the design for the present invention allows for one, some or all of the following functions: minimize spatial mapping and task sequences; eliminate the separate mixing containers; provide a closed environment to minimize fluid loss due to heating; separate and seal the multiple test areas on a slide; protect the substrate from accidental breaking; permit easy user handling; allow for individual access to each test to minimize mistakes; permit fast temperature changes; eliminate the need for centrifugation to condense fluid in one area; facilitate the signal amplification by blocking light; and be sterilized with gamma or e-beam.

Although certain presently preferred embodiments of the invention have been described herein, it will be apparent to those skilled in the art to which the invention pertains that variations and modifications of the described embodiment may be made without departing from the spirit and scope of the invention.

The invention claimed is:

1. Apparatus for DNA hybridization of probes on an upper surface of a substrate, the apparatus comprising:

a material for creating a seal against the substrate, wherein the material is pliable, wherein the material and the substrate are operable to form a plurality of chambers when the material abuts the substrate, wherein each chamber has a bottom that includes at least a portion of the upper surface, at least two sidewalls, and an opening, wherein the at least two sidewalls are at least partially curved where the at least two sidewalls meet; and a mechanism for closing the openings of the chambers, wherein when the material abuts against the substrate and the mechanism closes the openings of the chambers, the chambers are sealed.

2. The apparatus as claimed in claim 1, wherein the upper surface of the substrate includes a plurality of areas having probes, and wherein the bottom of each chamber includes at least one of the plurality of areas of probes.

3. The apparatus as claimed in claim 1, wherein each of the at least two sidewalls is at least partially curved.

4. The apparatus as claimed in claim 1, wherein the material further comprises a neck portion providing a conduit for fluid from the opening to an inner portion of the chamber, and wherein the neck portion has a first end connected to the opening and a second end connected to the inner portion.

5. The apparatus as claimed in claim 4, wherein the neck portion has an angle which is less than 180 degrees.

6. The apparatus as claimed in claim 5, wherein the angle is greater than 90 degrees and less than 180 degrees.

7. The apparatus of claim 4, wherein the second end of the neck portion is centered at a point which is not directly above a geometric center of an area enclosed within the at least two sidewalls.

8. The apparatus of claim 7, wherein the neck portion has an angle which is greater than 90 degrees and less than 180 degrees.

9. The apparatus of claim 1, wherein at least a portion of at least one of the two sidewalls are not perpendicular to the upper surface of the substrate.

10. The apparatus of claim 9, wherein at least a portion of at least one of the at least two sidewalls is curved.

11. The apparatus of claim 1, wherein the upper surface of the substrate has a plurality of areas having probes, and wherein the material further comprises at least one compression rib, whereby the compression rib abuts against the upper surface sealing at least one of the plurality of areas having probes.

12. The apparatus of claim 1, wherein the upper surface of the substrate has first and second areas, wherein the first and second areas have probes, wherein the material further comprises first and second compression ribs, wherein the first compression rib forms a seal about the first area, wherein the second compression rib forms a seal about the second area, wherein the second area is adjacent to the first area, and wherein an airspace is formed between the first compression rib, the second compression rib and the upper surface of the substrate.

13. The apparatus as claimed in claim 1, wherein the material comprises a silicone-based material.

14. The apparatus as claimed in claim 1, further comprising a rigid material abutting at least a portion of the material.

15. The apparatus as claimed in claim 14, further comprising an airspace formed between the rigid material and the material.

16. The apparatus as claimed in claim 15, wherein the airspace is formed between at least one sidewall of the at least two sidewalls and the rigid material, and wherein the at least one sidewall expands into the airspace responsive to an increase in pressure in the chamber when sealed, thereby allowing the chamber to remain sealed under the increased pressure.

17. The apparatus as claimed in claim 14, wherein the material further comprises an opening lip, wherein the opening lip being adjacent to the opening, and wherein the rigid material abuts at least a portion of the opening lip.

18. The apparatus as claimed in claim 14, wherein a ledge is formed in the material between the sidewalls of the chambers, and wherein the rigid material abuts at least a portion of the ledge of the material.

19. The apparatus as claimed in claim 18, wherein the rigid material comprises a beam, and wherein the beam abuts at least a portion of the ledge of the material.

20. The apparatus as claimed in claim 1, further comprising a rigid material abutting at least a portion of the substrate, wherein the rigid material provides support for the substrate.

21. The apparatus as claimed in claim 20, wherein the rigid material comprises a substrate holder.

22. The apparatus as claimed in claim 21, wherein the substrate holder comprises at least one spring and a datum point, the at least one spring for placing a portion of the substrate in the datum point of the substrate holder.

23. The apparatus as claimed in claim 22, wherein the substrate holder comprises means for placing the substrate in a predetermined position.

24. The apparatus as claimed in claim 21, further comprising a rigid material abutting at least a portion of the material, wherein the rigid material abutting at least a portion of the material is connected to the substrate holder.

25. The apparatus as claimed in claim 24, wherein the rigid material abutting at least a portion of the material is clamped to the substrate holder.

26. The apparatus as claimed in claim 1, wherein the mechanism for closing the openings comprises a part for independently closing each of the openings.

27. The apparatus as claimed in claim 1, wherein the mechanism for closing the openings comprises protrusions that can be inserted into the openings thereby sealing the chambers.

28. The apparatus as claimed in claim 27, further comprising a rigid material abutting at least a portion of the material, and wherein the protrusions are connected to the rigid material.

29. The apparatus as claimed in claim 27, wherein at least two protrusions are connected to one another.

30. The apparatus as claimed in claim 1, wherein the mechanism for closing the openings comprises a part for pinching the opening so as to seal the chambers.

31. The apparatus as claimed in claim 30, wherein the part of the mechanism for closing the openings comprises a rigid material with a v-shaped groove.

* * * * *

UNITED STATES PATENT AND TRADEMARK OFFICE

CERTIFICATE OF CORRECTION

PATENT NO. : 7,163,823 B2

APPLICATION NO. : 10/352714
DATED : January 16, 2007
INVENTOR(S) : Timothy Patno et al.

It is certified that error appears in the above-identified patent and that said Letters Patent is hereby corrected as shown below:

Title page
Item [75], Inventors, change “George Kyaw Soe Maung” to -- George Kyaw Soe Maung Aye --.

Signed and Sealed this

Twentieth Day of March, 2007

JON W. DUDAS
*Director of the United States Patent and Trademark Office*